US006994963B1

(12) United States Patent
Murphy et al.

(10) Patent No.: US 6,994,963 B1
(45) Date of Patent: Feb. 7, 2006

(54) METHODS FOR RECOMBINATORIAL NUCLEIC ACID SYNTHESIS

(75) Inventors: George L. Murphy, Austin, TX (US); Robert A. Setterquist, Austin, TX (US); Andrew D. Ellington, Austin, TX (US)

(73) Assignee: Ambion, Inc., Austin, TX (US)

( * ) Notice: Subject to any disclaimer, the term of this patent is extended or adjusted under 35 U.S.C. 154(b) by 701 days.

(21) Appl. No.: 09/613,535

(22) Filed: Jul. 10, 2000

(51) Int. Cl.
*C12Q 1/68* (2006.01)
*C12P 21/06* (2006.01)
*C12P 19/34* (2006.01)
*C07H 21/04* (2006.01)

(52) U.S. Cl. .................. 435/6; 435/69.1; 435/91.1; 435/91.51; 536/23.1; 536/23.5; 536/24.33

(58) Field of Classification Search .............. 435/91.1, 435/91.2, 91.21, 6, 69.1, 91.51; 536/23.1, 536/23.2, 23.5, 24.3, 24.33
See application file for complete search history.

(56) References Cited

U.S. PATENT DOCUMENTS

| | | | | |
|---|---|---|---|---|
| 4,865,968 A | * | 9/1989 | Orgel et al. ................. 204/462 |
| 5,106,585 A | * | 4/1992 | Minami et al. ............ 422/68.1 |
| 5,679,512 A | * | 10/1997 | Laney et al. ..................... 435/6 |
| 5,723,323 A | | 3/1998 | Kauffman et al. ........ 435/172.3 |
| 5,741,676 A | * | 4/1998 | Fuller ......................... 435/91.1 |
| 5,747,298 A | * | 5/1998 | Hong et al. ................. 435/91.1 |
| 5,830,655 A | * | 11/1998 | Monforte et al. .............. 435/6 |
| 5,965,408 A | | 10/1999 | Short ......................... 435/91.1 |
| 6,087,095 A | * | 7/2000 | Rosenthal et al. ............. 435/6 |
| 6,117,679 A | | 9/2000 | Stemmer .................... 435/440 |
| 6,132,970 A | | 10/2000 | Stemmer ....................... 435/6 |
| 6,153,410 A | * | 11/2000 | Arnold et al. ............. 435/91.2 |
| 6,159,687 A | | 12/2000 | Vind ............................. 435/6 |
| 6,165,793 A | | 12/2000 | Stemmer .................... 435/440 |
| 6,177,263 B1 | | 1/2001 | Arnold et al. ............. 435/91.1 |
| 6,180,406 B1 | | 1/2001 | Stemmer .................... 435/440 |
| 6,506,603 B1 | * | 1/2003 | Stemmer .................... 435/440 |
| 6,534,292 B1 | * | 3/2003 | Volkov ...................... 435/91.1 |

FOREIGN PATENT DOCUMENTS

| | | |
|---|---|---|
| WO | WO 97/20078 | 6/1997 |
| WO | WO 98/01581 | 1/1998 |
| WO | WO 98/05765 | 2/1998 |
| WO | WO 98/27230 | 6/1998 |
| WO | WO 98/32845 | 7/1998 |
| WO | WO 98/41622 | 9/1998 |
| WO | WO 98/41623 | 9/1998 |
| WO | WO 98/41653 | 9/1998 |
| WO | WO 98/42728 | 10/1998 |
| WO | WO 98/42832 | 10/1998 |
| WO | WO 98/58080 | 12/1998 |
| WO | WO 99/15698 | 4/1999 |
| WO | WO 99/20768 | 4/1999 |
| WO | WO 99/29882 | 6/1999 |
| WO | WO 99/47536 | 9/1999 |
| WO | WO 00/42561 | 7/2000 |

OTHER PUBLICATIONS

Altschul et al., "Basic Local Alignment Search Tool," *J. Mol. Biol.* 215:403-410, 1990.
Ambrose et al., "DNA Sequencing: Chemical Methods," "152:522-538, 1987.
Arkin et al., "An Algorithm for protein engineering: Simulations of recursive ensemble mutagenesis," *PNAS USA* 89: 7811-7815, 1992.
Barcak, et al., "A method for unidirectional deletion mutagenesis with application to nucleotide sequencing and preparation of gene fusions," *Gene,* 49:119-128, 1986.
Breaker et al., "Self-Incorporation of Coenzymes by Ribozymes," *J. Mol Evol.,* 40:551-558, 1995.
Caldwell and Joyce, "Mutagenic PCR," *PCR Methods and Applications,* 3:S136-S140, 1994.
Carbonelli et al., "A placid vector for isolation of strong promoters in *Eschirichia coli,*" *FEMS Microbiol Lett.,* 177: 75-82, 1999.
Chandler et al., "RNA splicing specificity determined by the coordinated action of RNA recognition motifs in SR proteins," *Proc Natl Acad Sci U S A.,* 94:3596-3601, 1997.
Chang et al., "Evolution of a cytokine using DNA family shuffling," *Nature Biotechnology,* 17:793-797, 1999.
Chapman and Szostak, "Isolation of a ribozyme with 5'- 5' ligase activity," *Chem Biol.* 2:325-333, 1995.
"Light based scissors cleave DNA," *Chemical and Engineering News,* Sep. 13, p 40, 1999.
Chen and Okayama, "High-Efficiency Transformation of Mammalian Cells by Plasmid DNA," *Mol. Cell. Biol.,* 7:2745-2752, 1987.
Chowrira et al., "In Vitro and in Vivo Comparison of Hammerhead, Hairpin, and Hepatitis Delta Virus Self-processing Ribozyme Cassettes," *J. Biol. Chem.,* 269: 25856-25864, 1994.

(Continued)

*Primary Examiner*—Kenneth R. Horlick
*Assistant Examiner*—Cynthia B. Wilder
(74) *Attorney, Agent, or Firm*—Fulbright & Jaworski

(57) ABSTRACT

This invention pertains to a method for generating a pool of nucleic acid fragments useful for in vitro recombination and the creation of novel DNA sequences that encode desirable proteins or enzymes. The invention provides a defined mixture of nucleic acids and methods for use in the synthesis, mutagenesis, and recombination of nucleic acids. Nucleic acids may be synthesized by creating a nucleic acid extension ladder, annealing the extension ladder to template nucleic acids, and further extending the ladder of nucleic acids. The invention also relates to methods for performing repeated cycles of synthesis for the purpose of mutagenesis or recombination, methods for producing mutant peptides and proteins from the mutagenized or recombined nucleic acids, and methods for selecting a peptide, polypeptide or protein having altered biological activities.

33 Claims, 4 Drawing Sheets

OTHER PUBLICATIONS

Cocea, "Duplication of a Region in the Multiple Cloning Site of a Plasmid Vector to Enhance Cloning-Mediated Addition of Restriction Sites to a DNA Fragment," *Biotechniques*, 23:814-816, 1997.

Crameri et al., "DNA shuffling of a family of genes from diverse species accelerates directed evolution," *Nature*, 391:288-291, 1998.

Crameri et al., "Improved Green Fluorescent Protein by Molecular Evolution Using DNA Shuffling," *Nature Biotechnology*, 14:315-319, 1996.

*Current Protocols in Molecular Biology.* Ed. F. M. Ausubel et al., vol. 1, 1996, Table of Contents.

Eun, "Enzymology Primer for Recombinant DNA Technology," *Academic Press*, 3:215-220, 1996.

Fechheimer et al., "Transfection of mammalian cells with plasmid DNA by scrape loading and sonication loading," *Proc. Natl. Acad. Sci., USA* 84:8463-8467, 1987.

Foder et al., "Light-Directed, Spatially Addressable Parallel Chemical Synthesis," *Science*, 251:767-773, 1991.

Fraley and Fornari Kaplan, "Entrapment of a bacterial plasmid in phospholipid vesicles: Potention for gene transfer," *Proc. Nat'l. Acad. Sci. USA*, 76:3348-3352, 1979.

Gish and Eckstein, "DNA and RNA sequencing utilizing phosphorothioate chemistry," *NAR Symp. Ser.*, 8:253-256, 1987.

Gopal, "Gene Transfer Method for Transient Gene Expression, Stable Transformation, and Cotransformation of Suspension Cell Cultures," *Mol. Cell. Biol.*, 5:1188-1190, 1985.

Graham and Van Der Eb, "A New Technique for the Assay of Infectivity of Human Adenovirus 5 DNA," *Virology*, 52:456-467, 1973.

Kaeppler et al., "Silicon carbide fiber-mediated DNA delivery into plant cells," *Plant Cell Reports*, 9: 415-418, 1990.

Kaneda et al., "Increased Expression of DNA Cointroduced with Nuclear Protein in Adult Rat Liver," *Science*, 243:375-378, 1989.

Kato et al., "Expression of Hepatitis B Virus Surface Antigen in Adult Rat Liver," *J. Biol. Chem.*, 266:3361-3364, 1991.

Labeit et al., "A New Method of DNA Sequencing Using Deoxynucleoside α-Thiotriphosphates," *DNA* 5:173-177, 1986.

Lee et al., "Ribozyme-catalyzed tRNA aminoacylation," *Nat Struct Biol.*, 7:28-33, 2000.

Leung et al., "A Method for Random Mutagenesis of a Defined DNA Segment Using a Modified Polymerase Chain Reaction," *Technique*, 1:11-15, 1989.

Lieber and Strauss, "Selection of Efficient Cleavage Sites in Target RNAs by Using a Ribozyme Expression Library," *Mol. Cell. Biol.*, 15:540-551, 1995.

Lohse and Szostak, "Ribozyme-catalysed amino-acid transfer reactions," *Nature.* 30:381:442-444, 1996.

Longo et al., "Use of uracil DNA glycosylase to control carry-over contamination in polymerase chain reactions," *Gene*, 93:125-128, 1990.

Lorsch and Szostak, "Kinetic and Thermodynamic Characterization of the Reaction Catalyzed by a Polynucleotide Kinase Ribozyme," *Biochemistry*, 34:15315-15327, 1995.

Macejak and Sarnow, "Internal initiation of translation mediated by the 5' leader of a cellular mRNA," *Nature*, 353:90-94, 1990.

Maxam and Gilbert, "Sequencing End-Labeled DNA with Base-Specific Chemical Cleavages," *Methods Enzymology*, 65:499-560, 1980.

Messing and Vieira, "A new pair of M13 vectors either DNA strand of double-digest restriction fragments," *Gene*, 19:269-276, 1982.

Moore and Arnold, "Directed evolution of a para-nitrobenzyl esterase for aqueous-organic solvents," *Nature Biotechnology*, 14:458-467, 1996.

Moore et al., "Strategies for the in vitro Evolution of Protein Function: Enzyme Evolution by Random Recombination of Improved Sequences," *J. Molecular Biol.*, 272:336-347, 1997.

Nicolau and Sene, "Lipsome-Mediated DNA Transfer in Eukaryotic Cells," *Biochem. Biophys. Acta*, 721:185-190, 1982.

Nicolau et al., "Liposomes as Carriers for in Vivo Gene Transfer and Expression," 149:157-176, 1987.

Nixon et al., "Hybrid enzymes: manipulating enzyme design," *Trends in Biotech.*, 16:258-264, 1989.

Ohuchi et al., "In vitro method for the generation of protein libraries using PCR amplification of a single DNA molecule and coupled transcription/translation," *NAR*, 26:4339-4346, 1998.

Oliphant, et al., "Cloning of random-sequence oligodeoxynucleotides," *Gene*, 44:177-183, 1986.

Ostermeier et al., "A combinatorial approach to hybrid enzymes independent of DNA homology," *Nature Biotechnology*, 17:1205-1209, 1999.

Ostermeier et al., "Combinatorial protein engineering by incremental truncation," *PNAS*, 96:3562-3567, 1999.

Pelletier and Sonenberg, "Internal initiation of translation of eukaryotic mRNA directed by a sequence derived from poliovirus RNA," *Nature*, 334:320-325, 1988.

Pompon & Nicolas, "Protein engineering by cDNA recombination in yeasts: shuffling of mammalian cytochrome P-450 functions," *Gene*, 83:15-24, 1989.

Pompon et al., "Protein engineering by cDNA recombination in yeasts: shuffling of mammalian cytochrome P-450 functions," *Gene*, 83:15-24, 1989.

Potrykus et al., "Direct gene transfer to cells of a graminaceous monocot," *Mol. Gen. Genet.*, 199:183-188, 1985.

Rippe et al., "DNA-Mediated Gene Transfer into Adult Rat Hepatocytes in Primary Culture," *Mol. Cell Biol.*, 10:689-695, 1990.

Sambrook et al., "Extraction of RNA with Guanidinium Thiocyanate Followed by Centrifugaiton in Cesium Chloride Solutions," In: Molecular Cloning: A Laboratory Manual, vol. 1, Cold Spring Harbor Laboratory Press, 7:7.19-17.29, 1989.

Scheit, *Nucleotide Analogs* John Wiley & Sons, New York, 1980.

Schulga et al., "An approach to construction of hybrid polypeptide molecules—homologue recombination method," *NAR* 22:3808-3810, 1994.

Shao et al., "Random priming in vitro recombination: an effective tool for directed evolution," *NAR* 26:681-683, 1998.

Skalski et al., "Removal of Anti-Human Immunodeficiency Virus 2', 3' Dideoxynucleoside Monophosphates from DNA by a Novel Human Cytosolic 3' → 5' Exonuclease," *Biochem. Pharmacol.*,50:815-821, 1995.

Stemmer, "Rapid evolution of a protein in vitro by DNA shuffling," *Nature*, 370:389-391, 1994.

Stemmer, "DNA shuffling by random fragmentation and reassembry: In vitro recombination for molecular evolution," *PNAS,* 91:10747-10751, 1994.

Vita, "Engineering novel proteins by transfer of active sites to natural scaffolds," *Current Opinion in Biotechnology,* 8:429-434, 1997.

Weber et al., "Formation of genes coding for hybrid proteins by recombination between related, cloned genes in *E. coli,*" *NAR,* 11:5661-5669, 1983.

Wilson C. and Szostak, "In vitro evolution of a self-alkylating ribozyme," *J.W. Nature,* 374:777-782, 1995.

Wong et al., "Appearance of a β- lactamase activity in animal cells upon liposome-mediated gene transfer," *Gene,* 10:87-94, 1980.

Zhao et al., "Optimization of DNA shuffline for high fidelity recombination," *NAR,* 25:1307-1308, 1997.

Zhao et al., "Molecular evolution by staggered extension process (StEP) in Vitro recombination," *Nature Biotechnology,* 16:258-261, 1998.

* cited by examiner a) ribonucleotide (NTP)
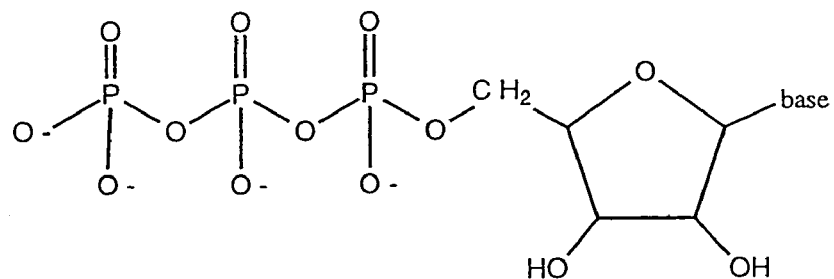
b) deoxyribonucleotide (dNTP)
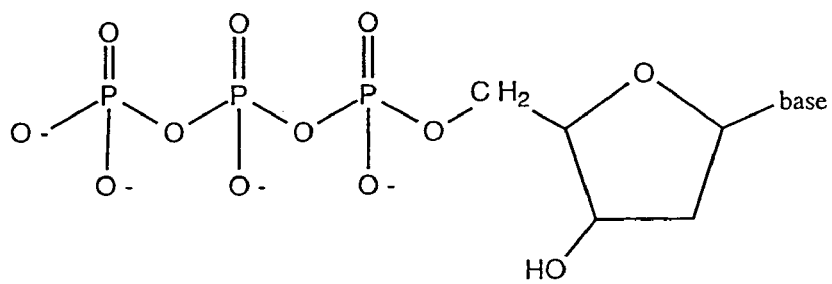
c) dideoxyribonucleotide (ddNTP)
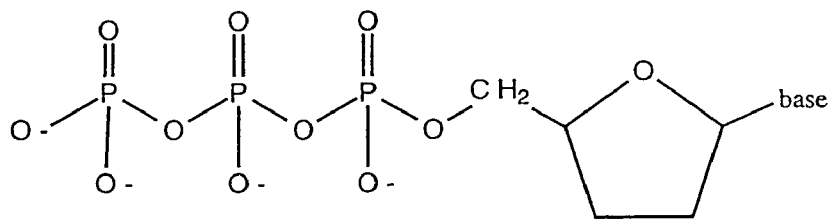
d) deoxyribonucleotide[1-thio]triphosphate
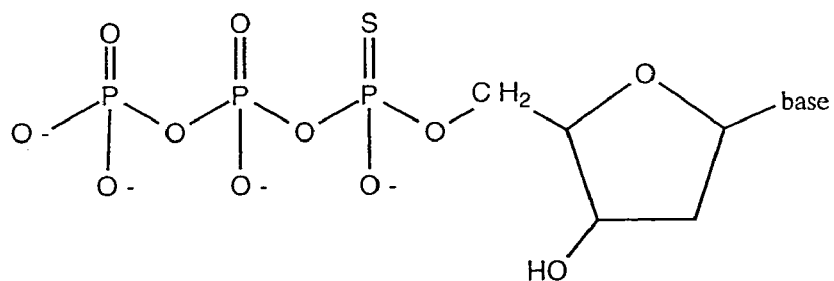
Fig. 4

SEQUENCE LISTING

<160> NUMBER OF SEQ ID NOS: 5

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 1
gttttcccag tcacgacgtt gta                                           23

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: modified_base
<222> LOCATION: (24)..(28)
<223> OTHER INFORMATION: Thioester exists  between these positions

<400> SEQUENCE: 2
gttttacaac gtcgtgactg ggaaaacc                                      28

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 3
ggttttccca gtcacgacgt tgta                                          24

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: modified_base
<222> LOCATION: (24)..(28)
<223> OTHER INFORMATION: Thioester exists between these positions -continued

```
<400> SEQUENCE: 4
gttggacaac gtcgtgactg ggaaaacc                                            28

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:  Synthetic
      Primer
<220> FEATURE:
<221> NAME/KEY: modified_base
<222> LOCATION: (16)..(19)
<223> OTHER INFORMATION: Thioester exists between these positions
<220> FEATURE:
<221> NAME/KEY: modified_base
<222> LOCATION: (24)..(24)
<223> OTHER INFORMATION: Diodeoxy cytosine exists at this position

<400> SEQUENCE: 5
ggttttccca gtcacgacgt tgtc                                                24
```

METHODS FOR RECOMBINATORIAL NUCLEIC ACID SYNTHESIS

BACKGROUND OF THE INVENTION

1. Field of the Invention

This invention relates to the field of molecular biology and recombinant nucleic acid technology. Specifically, this invention pertains to a method for generating a pool of nucleic acid fragments useful for in vitro recombination and the creation of novel nucleic acid sequences that encode potentially desirable proteins or enzymes.

2. Description of Related Art

DNA sequence databases are growing exponentially with the submission of entire genome sequences. By inference, gene sequences create protein databases consisting of the amino acid sequences deduced from all the sequenced genes. DNA and protein sequence searches have provided information about the function and structure of proteins from novel gene sequences. Proteins that share sequence similarity are classified in "families". The basis of these analyses is that sequence similarity can imply homology and common function.

Enzymes within a protein family may have similar catalytic activities, although unique characteristics of different enzymes may vary widely. Although several proteins in a family may have the same general function, conditions for optimal activity can be very different for each individual protein. The fundamental differences between enzymes are due to variations in their naturally evolved three-dimensional structure, which is ultimately determined by the linear amino acid sequence. Therefore, embedded within the sequences of proteins are functional folds, which in theory could exist, in numerous, yet undiscovered combinations, producing enzymes with different activities.

Many biotechnological processes exist for which there is a need for enzymes with increased stability, enhanced activity and new catalytic functions. Using the knowledge of previous structural and functional determinations, the current state of biotechnology does not allow one to design an enzyme de novo. To overcome this limitation, enzymes with new traits can be engineered by altering the structure of defined domains in natural proteins via specific mutagenesis or by random mutagenesis methods such as "gene shuffling". An entire spectrum of mutational types are available through protein engineering, including single amino acid changes, multiple amino acid changes, segment replacements, whole domain swapping, and entire protein fusion.

The ability to make predetermined amino acid changes (i.e., site-directed mutagenesis) that will alter an enzyme's catalysis in a predictable manner requires extensive information about the enzymatic mechanism and those structural features of the protein which impart catalysis. The difficulties associated with rational mutagenesis for altering an enzyme's activity are in large part due to the unpredictable, balanced interactions among hundreds of amino acid side chains with each other, cofactors, water, substrate, and product. Therefore, significant changes in an enzyme's stability or activity are much more difficult to design through single mutations. Furthermore, when multiple substitutions are required, the number of possibilities is enormous, determined by the formula $20^N$ where N is the number of amino acids in the protein, assuming that only the 20 commonly occurring amino acids are used.

Today, in vitro evolution methodologies may be used to alter an enzyme's structure. Using these types of methods numerous groups have engineered enzymes with altered or enhanced activities (Stemmer, 1994; Crameri et al., 1998; Moore & Arnold, 1996; Moore et al., 1997). Random alteration of gene sequences can be a powerful method for creating pools of proteins with different enzymatic capabilities. With appropriate assays, one can screen or select those enzymes with the desired activity. Current methods for creating such pools include error-prone PCR (Leung et al., 1989; Caldwell and Joyce, 1992), cassette mutagenesis (Arkin, A. & Youvan, D. C., 1992; Oliphant, A. R. et al., 1986), hybrid enzyme generation (Ostermeier et al., 1999a), in vivo recombination (Pompon & Nicolas, 1989), gene shuffling (Stemmer, 1994), and the Staggered Extension Process (StEP) (Zhao et al., 1998).

In error-prone PCR, altering the reaction conditions reduces the fidelity of the polymerase reaction. Typically this is accomplished by increasing the concentration of magnesium chloride, adding manganese chloride, increasing and unbalancing the dNTP concentrations, increasing the concentration of Taq polymerase, and/or increasing the extension time. The most error-prone conditions produce a 2% mutation rate per position and more typically about a 0.7% mutation rate per position. An advantage of error-prone PCR is that any gene fragment can be mutagenized. However, point mutations alone are thought to be too gradual for significant gene alterations and frequently result in neutral substitutions.

Cassette mutagenesis and domain swapping target defined regions of a protein. A cassette may be synthesized with a predetermined amount of degeneracy, from completely random to single amino acid change, in a defined length of the protein. Domain swapping refers to the creation of hybrid proteins having one or more domain from different proteins. If a protein domain is defined in a linear segment of amino acids, the domain may easily be inserted or substituted in other homologous proteins. Structural information is usually necessary for defining and swapping domains. A domain may be the active site of an enzyme. Transfer of active sites to homologous proteins may also lead to enzymes with new activities (Vita, C., 1997). Domain mutagenesis is not restricted to swapping of homologous domains, but also includes domain insertion to create multifunctional activities or control enzymes (Nixon et al., 1989). However, cassette mutagenesis is limited by the need to know sequence or domain boundaries and to the mutagenesis of a specific region, such as a region encoding a contiguous sequence of amino acids.

Domain swapping effectively performed without prior knowledge of domain boundaries has been described (Ostermeier et al., 1999a; Ostermeier et al., 1999b; Schulga et al., 1994). This has been termed as the incremental truncation for the creation of hybrid enzymes (ITCHY) (Ostermeier et al., 1999b). In this method, a library of 5' fragments of random length from one gene is fused with a library of 3' fragments of random length from another gene. The fragments are created by limited Exonuclease III digestion. Aliquots of an exonuclease digestion mixture are removed at short intervals to create a series of different length fragments. The fragments are joined in a plasmid vector, which can then be used to express the fusion protein. Hybrid enzymes may utilize established functions or properties from a wild-type enzyme and incorporate them into a novel enzyme (Nixon et al., 1989). ITCHY libraries are limited to one crossover point per hybrid.

In vivo recombination may also facilitate genetic modifications and mutations. Different vector systems and host strains have been described (WO 99/29902; Weber et al., 1983; Pompon et al., 1989).

The procedure referred to as "gene shuffling" or "sexual PCR" closely approximates the evolutionary process. In this method, parental genes are fragmented and reassembled by PCR™ to create full-length genes (U.S. Pat. Nos. 5,605,793; 5,811,238; 5,830,721). The shuffling procedure typically starts with double-stranded nucleic acid fragments such as PCR™ products from homologous genes. The genes are cleaved, for example with DNAse I, to produce random fragments. The fragments are purified and reassembled in PCR™ without primers. As the random fragments and their PCR™ products prime each other, the average size of the fragments increases with the number of PCR™ cycles. Recombination or crossover occurs by template switching, such as when a DNA fragment derived from one template primes on the homologous position of a related but different template. Products of the PCR™ undergo a second amplification reaction using primers from the original reaction. Full-length fragments are cloned into an expression vector for selection and screening. Reiterative rounds of this process are continued until the desired protein is found or no further improvements are achieved. Examples of enzyme improvements following gene shuffling have been reported (Crameri et al., 1996; Chang et al., 1999; Crameri et al., 1998). However, these methods generally involve optimization of nucleic acid fragmentation, size fractionation, or purification of gene fragments.

A modification of gene shuffling, the Staggered Extension Protocol (StEP) has been described (WO 98/42832; Shao et al., 1998; Zhao et al., 1997; Zhao et al., 1998). StEP involves priming template polynucleotides with random or flanking primers. Extended primers are reassembled in extremely fast cycles of PCR™, generating successively longer and longer extension products. In each cycle the primers/extension products can anneal to different templates based on sequence complementarity. The template switching between different sequences creates "recombination cassettes". The process is continued until full-length genes are created. However, StEP requires careful monitoring of polymerase extension by precisely controlling time and temperature of the reaction.

A modification of the StEP technology has also been described (U.S. Pat. No. 5,965,408). Like StEP, random primers are annealed to a target(s) to be shuffled. The random primers are extended until stopped by "roadblocks" such as purine dimers. The premature termination is facilitated by blocking the polymerase with adducts associated with the template. Fragments are isolated and used in a separate PCR™ reaction to create longer overlapping fragments. However, the use of DNA adducts to create "roadblocks" may result in the halting of DNA synthesis at preferred locations of adduct binding. Therefore, halting of DNA synthesis may not randomly occur along the length of the nucleic acid and may not occur at every nucleotide in a sequence.

Despite these techniques for mutating nucleic acids and encoded polypeptides, there still exists a need for improved mutagenesis techniques. Methods that are easy, rapid, and result in thorough mutation of one or more sequences would be desirable.

SUMMARY OF THE INVENTION

The present invention overcomes the limitations of past methods by simultaneously bringing together all the advantages imparted by incremental truncation for the creation of hybrid enzymes with the mutagenic and recombinatorial processes of StEP. Furthermore, the present invention may use a complete library of nucleic acid extension products that differ in length by a single base. As a result, recombinatorial mutagenesis results in recombined sequences with potential crossover points at every single nucleotide in a nucleic acid sequence. Of course, the methods of the present invention may also be combined with other techniques known in the art, such as for example, error-prone PCR™, cassette mutagenesis, sexual PCR™, ITCHY or StEP in the production of altered or new nucleic acid sequences.

The invention provides a method for producing a nucleic acid, comprising the steps of: (a) annealing at least one primer nucleic acid to at least one template nucleic acid, (b) performing a first extension by extending the primer nucleic acid employing the template nucleic acid to form an extended nucleic acid, (c) cleaving the at least one extended nucleic acid, wherein the cleaved extended nucleic acid comprise a nucleic acid extension ladder; (d) denaturing the extended nucleic acid from the template nucleic acid, (d) annealing the extended nucleic acid to at least a second template nucleic acid, (e) performing at least a second extension by extending the extended nucleic acid employing the second template nucleic acid to form a twice extended nucleic acid, (f) adding at least one chain-terminating agent comprising at least one dideoxynucleotide, a dideoxynucleotide analog or a dideoxynucleotide derivative before or during at least one of the first extension or the second extension, wherein said chain-terminating agent is incorporated into said extended nucleic acid, and (g) modifying or removing the chain-terminating agent from the extended nucleic acid, if a further extension is to be performed.

In certain embodiments, a method of the present invention further comprises: (a) denaturing a twice extended nucleic acid from a second template nucleic acid, (b) annealing the twice extended nucleic acid to a third template nucleic acid, and (c) performing at least a third extension by extending the twice extended nucleic acid employing the third template nucleic acid to form a thrice extended nucleic acid. In some aspects, the method comprises adding at least one chain-terminating agent comprising at least one ddNTP (e.g., ddATP, ddCTP, ddGTP, ddTTP, or other dideoxy nucleotide, analog or derivative) before or during the third extension. In further aspects, the method comprises adding at least one chain-terminating agent comprising at least one ddNTP (e.g., ddATP, ddCTP, ddGTP, ddTTP, or other dideoxy nucleotide, analog or derivative) before or during the any additional extension.

Some methods of the present invention may comprise the addition of at least one length-altering agent before, during or after a step of a method of the invention. In certain aspects, a length-altering agent comprises a nucleotide, a nucleotide derivative, a nucleotide analog, a chemical treatment or a combination thereof. In preferred aspects, the length-altering agent comprises a chain-terminating agent (e.g., ddATP, ddCTP, ddGTP, ddTTP, or other dideoxy nucleotide, analog or derivative). In a non-limiting example, the addition of at least one chain-terminating agent occurs before, during or after the synthesizing. In another example, the addition of at least one chain-terminating agent occurs before, during or after the extending. In an additional example, at least one chain-terminating agent comprising at least one ddNTP (e.g., ddATP, ddCTP, ddGTP, ddTTP, or other dideoxy nucleotide, analog or derivative) is added before or during each extension. Usually, the length-altering agent (e.g., a chain-terminating agent) is removed from the extended nucleic acid, such as for example, by the action of at least one exonuclease. Removal of the length-altering agent allows further extension of the extended nucleic acid. In a non-limiting example, a chain-terminating agent is removed before, during or after the synthesizing step and/or the extending step. In other aspects, the at least one extension is performed without the addition of a length-altering agent (e.g., a chain-terminating agent).

In other aspects, a length-altering agent comprises a nucleotide incorporated into the extended nucleic acid, such as, for example, at least one ribonucleotide (e.g., ATP, CTP, GTP, UTP, a ribonucleotide derivative, a ribonucleotide analog, or a combination thereof). In particular facets, such a length-altering agent further comprises treatment with an alkaline condition or a ribonuclease. In other facets, a length-altering agent further comprises treatment with alkaline phosphatase and an exonuclease. In certain aspects, a length-altering agent comprises a nucleotide derivative incorporated into the extended nucleic acid.

In additional aspects, a length-altering agent comprises a nucleotide analog incorporated into the extended nucleic acid, such as for example, at least one α-phosphorothioate nucleotide (e.g., ATP-alpha-S, CTP-alpha-S, GTP-alpha-S, TTP-alpha-S, dATP-alpha-S, dCTP-alpha-S, dGTP-alpha-S, dTTP-alpha-S; Amersham). In particular facets, such a length-altering agent further comprises alkylation of the extended nucleic acid.

In some aspects, a length-altering agent comprises a chemical treatment of the extended nucleic acid, such as, for example, a Maxam and Gilbert treatment or variant thereof. Such treatments are understood by those of skill in the art.

In a preferred embodiment, a method of the present invention comprises repeating one or more steps (e.g., an annealing, performing, denaturing, adding, removing, synthesizing, hybridizing, cleaving, extending or additional step) contained in the method, in any order or combination. In a particular aspect, a method will comprise more than one step. In a non-limiting example, a method of the invention may comprise at least one annealing, performing, denaturing, adding, removing, synthesizing, hybridizing, cleaving, extending and/or additional step. In another example, the method may comprise at least one additional series of steps, such as for example, denaturing from a template, annealing to a further template, and performing of extension. In some aspects, the at least one additional series may be further defined as comprising between about two and about one hundred additional series of denaturing from a template, annealing to a further template, and performing of extension. In another example a method may comprise repeating a performing, extending and/or synthesizing step. In another example, the method may comprise repeating all the steps of a method. In a further example, a method may comprise repeating some of the steps of a method, such as for example, a denaturing, adding, removing and performing steps. In an additional example, a method may comprise repeating, for example, a denaturing, hybridizing and extending steps.

In some facets, one or more steps of a method are repeated in a cycle. Thus, a method may comprise at least one cycle of repeated steps. The number of times a step or cycle of steps may be repeated is not limited, however, in particular aspects a step or cycle of steps may be repeated about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 110, about 125, about 150, about 175, about 200, about 250, about 300, about 350, about 400, about 450, about 500, about 550, about 600, about 650, about 700, about 750, about 800, about 850, about 900, about 950, about 1000 or more times, and any range derivable therein. As used herein, "any range derivable therein" means a range selected from the numbers described in the specification.

In other embodiments, a primer nucleic acid comprises a sequence designed to anneal to a specific sequence comprising the template nucleic acid. In some aspects, a primer nucleic acid is resistant to cleavage or exonuclease digestion. In other aspects, the at least one primer nucleic acid is a plurality of primers. In certain facets, the plurality of primers vary in size, sequence, resistance to cleavage or resistance to exonuclease degradation.

In certain aspects, the primer may comprise a sequence of identity or a sequence of identity and a sequence of heterology to a template nucleic acid. In other aspects the template and primer may be incubated with agents, including but not limited to, one or more polymerases, and one or more length-altering agents.

In particular embodiments, the first template nucleic acid, the second template nucleic acid, the third template nucleic acid and/or an additional template nucleic acid have the same sequence.

The invention additionally provides a nucleic acid produced by a method of the present invention. In some embodiments, more than one or a plurality of extended nucleic acids are produced. One embodiment of the invention describes a mixture of nucleic acid molecules, such as but not limited to a nucleic acid extension ladder, to be used for producing a mutagenized or a chimerized nucleic acid by recombinatorial nucleic acid synthesis. In other aspects, a plurality of extended nucleic acids vary in size, sequence, resistance to cleavage and/or resistance to exonuclease degradation. In a specific facet, for example, a plurality of extended nucleic acids comprises nucleic acids of different sequence. In certain facets, a sequence of a plurality of extended nucleic acids varies by one nucleotide from another extended nucleic acid or a template nucleic acid. Similarly, a plurality of extended nucleic acids may comprise one or more extended nucleic acids that comprise different lengths relative to at least one member of the plurality or a template nucleic acid. In a particular facet, the different lengths comprise one nucleotide increments of variation relative to at least one member of the plurality or a template nucleic acid. In other facets, the different lengths comprise more than one nucleotide increments.

In some aspects, a nucleic acid extension ladder may be used in recombinatorial nucleic acid synthesis. In a preferred embodiment, a nucleic acid extension ladder may be produced by including a length-altering agent (e.g., a dideoxyribonucleotide) during nucleic acid synthesis from the end of an annealed primer, thereby resulting in the production of a partially double-stranded nucleic acid. The use of a defined pool of one or more partially double-stranded nucleic acids in recombinatorial nucleic acid synthesis is novel and can result in recombined sequences with potential crossover points at every single nucleotide in a nucleic acid sequence.

In a preferred aspect, the crossover points provide recombination, mutation or chimerization of at least one template nucleic acid.

In certain embodiments, an extended nucleic acid comprises at least one partly double stranded nucleic acid or at least one fully double stranded nucleic acid. In particular embodiments, the method or a step of a method of the present invention will produce a double-stranded nucleic acid. In some aspects, an extended nucleic acid comprises the primer nucleic acid. In other aspects of the present invention, a nucleic acid produced will comprise 5' end sequences derived from a primer. In an aspect, the length-altering agent is incorporated at least at the 3' end of the at least one nucleic acid.

In particular facets, an extended nucleic acid is a recombinant, mutagenized or chimeric nucleic acid. In other facets, the at least one template nucleic acid or the at least a second template nucleic acid vary in size, sequence, resistance to cleavage or resistance to exonuclease degradation. In additional facets, the at least one template nucleic acid or the at least a second template nucleic acid is a plurality of template nucleic acids.

The invention additionally provides a method for producing a mutant or chimeric peptide, polypeptide or protein by expressing or synthesizing a recombinant nucleic acid, peptide, polypeptide or protein encoded by a mutant or a chimeric nucleic acid produced by the methods of the present invention. As used herein, a "proteinaceous composition" generally refers, but is not limited to, a protein of greater than about 200 amino acids or the full length endogenous sequence translated from a gene; a polypeptide of greater than about 100 amino acids; and/or a peptide of from about 3 to about 100 amino acids. The invention thus provides a method for selecting nucleic acid(s), peptide(s), polypeptide(s) or protein(s) having altered biological activities.

The invention also provides a proteinaceous composition encoded by a nucleic acid produced by a method of the present invention. In certain embodiments, the proteinaceous composition comprises an enzyme. In other embodiments, a proteinaceous composition comprises a protein, a polypeptide or a peptide.

The invention provides a method for creating a nucleic acid comprising the steps of: (a) annealing at least one primer nucleic acid to at least one template nucleic acid, (b) performing a first extension by extending the primer nucleic acid employing the template nucleic acid to form an extended nucleic acid, (c) denaturing the extended nucleic acid from the template nucleic acid, (d) annealing the extended nucleic acid to at least a second template nucleic acid, (e) performing at least a second extension by extending the extended nucleic acid employing the second template nucleic acid to form a twice extended nucleic acid, (f) adding at least one length-altering agent before or during at least one of the first extension or the second extension, and (g) modifying or removing the length-altering agent from the extended nucleic acid, if a further extension is to be performed.

In a presently preferred specific embodiment, the invention provides a method for creating a nucleic acid comprising the steps of: (a) annealing at least one primer nucleic acid to at least one template nucleic acid, (b) performing a first extension by extending the primer nucleic acid employing the template nucleic acid to form an extended nucleic acid, (c) denaturing the extended nucleic acid from the template nucleic acid, (d) annealing the extended nucleic acid to at least a second template nucleic acid, (e) performing at least a second extension by extending the extended nucleic acid employing the second template nucleic acid to form a twice extended nucleic acid, (f) adding at least one chain-terminating agent comprising at least one ddNTP (e.g., ddATP, ddCTP, ddGTP, ddTTP, or other dideoxy nucleotide, analog or derivative) before or during at least one of the first extension or the second extension, and (g) modifying or removing the chain-terminating agent from the extended nucleic acid, if a further extension is to be performed. One example of this embodiment is shown in FIG. 1.

The invention provides a method for creating a nucleic acid comprising the steps of: (a) annealing at least one primer nucleic acid to at least one template nucleic acid, (b) synthesizing at least one extended nucleic acid from the primer nucleic acid, (c) denaturing the extended nucleic acid from the template nucleic acid, (d) hybridizing the extended nucleic acid to at least a second template nucleic acid, and (e) extending the extended nucleic acid, wherein at least length-altering or chain-terminating agent is added before or during the annealing, synthesizing, denaturing, hybridizing, or extending, and wherein the length-altering or chain-terminating agent is incorporated into the extended nucleic acid.

In another preferred specific embodiment, the invention provides a method for creating a nucleic acid comprising the steps of: (a) annealing at least one primer nucleic acid to at least one template nucleic acid, (b) performing a first extension by extending the primer nucleic acid employing the template nucleic acid to form an extended nucleic acid, (c) denaturing the extended nucleic acid from the template nucleic acid, (d) annealing the extended nucleic acid to at least a second template nucleic acid, (e) performing at least a second extension by extending the extended nucleic acid employing the second template nucleic acid to form a twice extended nucleic acid, (f) adding at least one length-altering agent before or during at least one of the first extension or the second extension, wherein said length-altering agent comprises at least one ribonucleotide (e.g., ATP, CTP, GTP, UTP, a ribonucleotide derivative, a ribonucleotide analog, or a combination thereof), and (g) modifying or removing the length-altering agent from the extended nucleic acid, if a further extension is to be performed. One example of this aspect of the invention is shown in FIG. 2.

In some embodiments, the invention provides a method for creating a nucleic acid comprising the steps of: (a) annealing at least one primer nucleic acid to at least one template nucleic acid, (b) performing a first extension by extending the primer nucleic acid employing the template nucleic acid to form an extended nucleic acid, (c) denaturing the extended nucleic acid from the template nucleic acid, (d) annealing the extended nucleic acid to at least a second template nucleic acid, (e) performing at least a second extension by extending the extended nucleic acid employing the second template nucleic acid to form a twice extended nucleic acid, (f) adding at least one length-altering agent before or during at least one of the first extension or the second extension, wherein said length-altering agent comprises at least one nucleotide analog incorporated into said extended nucleic acid followed by alkylation of said extended nucleic acid, and (g) modifying or removing the length-altering agent from the extended nucleic acid, if a further extension is to be performed. One example of this embodiment of the invention is shown in FIG. 3.

In other embodiments, the invention additionally provides a method for creating a nucleic acid comprising the steps of: (a) annealing at least one primer nucleic acid to at least one template nucleic acid, (b) performing a first extension by extending the primer nucleic acid employing the template nucleic acid to form an extended nucleic acid, (c) denaturing the extended nucleic acid from the template nucleic acid, (d) annealing the extended nucleic acid to at least a second template nucleic acid, (e) performing at least a second extension by extending the extended nucleic acid employing the second template nucleic acid to form a twice extended nucleic acid, (f) adding at least one length-altering agent before or during at least one of the first extension or the second extension, wherein said length-altering agent comprises at least one Maxam and Gilbert treatment or variant thereof, and (g) modifying or removing the length-altering agent, if a further extension is to be performed.

A product recombinant, mutagenized or chimeric nucleic acid obtainable by process (i.e., a method) for creating a nucleic acid described herein.

Use of a product recombinant, mutagenized or chimeric nucleic acid for purpose of producing a coding sequence encoding an enzyme, a ribozyme or an aptamer.

Use of a product recombinant, mutagenized or chimeric nucleic acid for purpose of producing a nucleic acid extension ladder, a ribozyme or an aptamer.

As used herein, "a method for creating a nucleic acid" will have the same meaning, and is interchangeable with, "a method for manufacturing product nucleic acid."

As used herein the specification, "a" or "an" may mean one or more. As used herein in the claim(s), when used in conjunction with the word "comprising", the words "a" or "an" may mean one or more than one.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A The nucleic acid extension ladders generated from two templates after the first round of extension in the presence of a chain-terminating agent, ddNTPs (dd) in this example. The length of terminated products can range from the length of the primer plus one base to a length equal to that of the template nucleic acid.

FIG. 1B Regeneration of extendable 3' ends on nucleic acid extension ladder products.

FIG. 1C Annealing of nucleic acid extension ladder to templates and synthesis.

FIG. 1D Recombined nucleic acids after multiple cycles of the invention method.

FIG. 2A The nucleic acid extension ladder generated from two templates (A and B) after a first round of extension in the presence of one or more ribonucleotide triphosphates (r). NTPs may be incorporated throughout the length of the extended nucleic acid.

FIG. 2B Generation of nucleic acid extension ladder by chemical or enzymatic cleavage. The length of members of the extension ladder may range from the length of the primer plus one base to a length equal to that of the template nucleic acid.

FIG. 2C Regeneration of extendable 3' ends on nucleic acid extension ladder with Exonuclease III (optional capture of A1/A2 and B1/B2 extension products).

FIG. 2D Annealing of nucleic acid extension ladder members to templates and extension. The annealing and priming allow the production of the next round of extension using A and B extension ladder products.

FIG. 2E Recombined nucleic acids after multiple cycles (a–d) of the invention method.

FIG. 3A The nucleic acid extension ladder generated from two templates (A and B) after a first round of extension in the presence of one or more phosphorothioated dNTPs (S). Phosphorothioated dNTPs may be incorporated throughout the length of the extended nucleic acids.

FIG. 3B Generation of nucleic acid extension ladder by chemical or enzymatic cleavage. The length of members of the extension ladder may range from the length of the primer plus one base to a length equal to that of the template nucleic acid.

FIG. 3C Regeneration of extendable 3' ends on nucleic acid extension ladder with Exonuclease III (optional capture of A1/A2 and B1/B2 extension products).

FIG. 3D Annealing of nucleic acid extension ladder members to templates and extension. Annealing and priming of the next round of extension uses A and B extension ladder products.

FIG. 3E Recombined nucleic acids after multiple cycles (a–d) of the invention method.

FIGS. 4A, 4B, 4C and 4D The structures of several different nucleotide triphosphates that may be used in nucleic acid synthesis.

FIG. 4A A ribonucleotide is 3' extendable and forms bonds that are susceptible to alkaline hydrolysis.

FIG. 4B A deoxyribonucleotide is 3' extendable and forms bonds that are susceptible to exonucleolytic cleavage.

FIG. 4C A dideoxyribonucleotide is not 3' extendable and forms bonds that are susceptible to exonucleolytic cleavage.

FIG. 4D A deoxyribonucleotide [1-thio] triphosphate is 3' extendable is resistant to most nucleolytic degradation, and forms bonds that are susceptible to chemical cleavage.

DESCRIPTION OF ILLUSTRATIVE EMBODIMENTS

Figure 1:
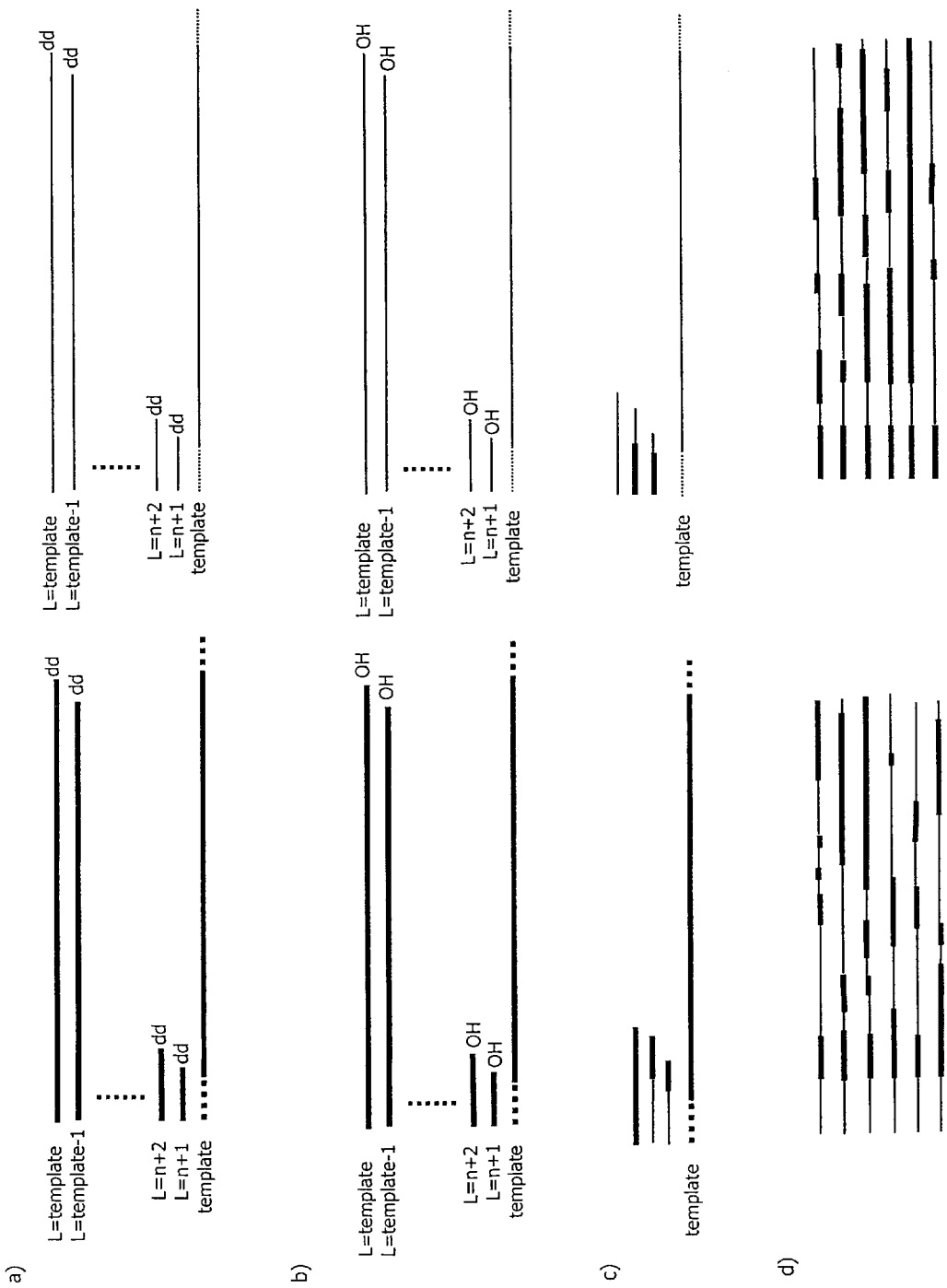
FIGS. 1A, 1B, 1C and 1D Selected steps involved in the synthesis of nucleic acid sequences.

Previously described methods of mutagenesis, such as ITCHY library production, are limited to one crossover point per hybrid. Additionally, other methods for mutagenesis and hybrid nucleic acid production require size fractionation of shuffled or recombined templates or priming nucleic acids, or requires monitoring or optimization of nucleic acid fragmentation, enzymatic degradation, or polymerase extension.

The method of the present invention provides for both multiple and single crossover events. Unlike other methods for mutagenesis and hybrid nucleic acid production, the present invention requires no size fractionation of nucleic acids (as in DNA shuffling methods) or recombined templates or priming nucleic acids at any step of the invention. The present invention does not require monitoring or optimization of nucleic acid fragmentation, enzymatic degradation, or polymerase extension. In particular, no monitoring of polymerization (as in StEP), exonucleolytic degradation (as in ITCHY), or nuclease digestion of template nucleic acids (as in other DNA shuffling methods) is required.

This invention relates to methods involving the production of nucleic acids for in vitro evolutionary gene mutagenesis. Using a process similar to evolution for creating amino acid changes and allowing selection and screening procedures to uncover the desired "evolved" molecule can alleviate the difficulties of rational mutagenesis. The assumption is that nature has narrowed through natural selection the allowable protein sequence space, and by starting within this space the chances of creating functional proteins is increased.

The invention also provides a defined mixture of nucleic acids and methods for use in the synthesis, mutagenesis, and/or recombination of nucleic acids. In one embodiment, nucleic acids may be synthesized by creating a nucleic acid extension ladder. As used herein, the term "nucleic acid extension ladder" means a mixture or a pool of single-stranded nucleic acids that differ in length and are derived after nucleic acid synthesis (extension) from the end of a primer nucleic acid after annealing of the primer nucleic acid to a template nucleic acid. Nucleic acid extension ladders with members that differ in length by a single nucleotide can be easily generated for any template. The members of nucleic acid extension ladders can be precisely defined and altered by defining and altering the components and agents used for steps of the invention, including but not limited to annealing the extension ladder to template nucleic acids, and further extending the ladder of nucleic acids. The present invention may produce and/or use a complete library of nucleic acid extension products that differ in length by a single base. The recombinatorial mutagenesis of the present invention can produce recombined sequences with potential crossover points at every single nucleotide in a nucleic acid sequence.

The present invention meets the need for enhanced methods for creating pools of nucleic acids with varying combinatorial complexities. The invention allows for easy generation of one or more simple hybrid libraries through the use of two or more different templates of nucleic acids, as well as very complex and degenerate multiple template-recombined libraries of nucleic acids. A simple control of the recombination frequency is imparted by the number of cycles that are chosen to be performed.

The invention also relates to methods for two or more repeated cycles of mutagenesis and/or recombination. A few cycles may result in simple recombined hybrid nucleic acids while each successive round will generate more interspersed mutations and sequence recombinations. In this way targeted and random mutagenesis is possible.

A. Primer and Template Nucleic Acids

The present invention involves the synthesis and/or mutation of at least one nucleic acid. Nucleic acid primers, templates, and analogues are used in the methods and compositions of the invention to produce and/or mutate one or more nucleic acid strands. Various nucleic acid compositions and methods that can be used in the present invention are described herein below.

The term "nucleic acid" will generally refer to at least one molecule or strand of DNA, RNA or a derivative or analog thereof, comprising at least one nucleobase, such as, for example, a naturally occurring purine or pyrimidine base found in DNA (e.g., adenine "A," guanine "G," thymine "T" and cytosine "C") or RNA (e.g., A, G, uracil "U" and C). A nucleobase generally can form one or more hydrogen bonds ("anneal" or "hybridize") with at least one naturally occurring nucleobase in a manner that may substitute for naturally occurring nucleobase pairing (e.g., the hydrogen bonding between A and T, G and C, and A and U).

As used herein, "nucleoside" refers to an individual chemical unit comprising a nucleobase covalently attached to a nucleobase linker moiety. A non-limiting example of a "nucleobase linker moiety" is a sugar comprising 5-carbon atoms (a "5-carbon sugar"), including but not limited to deoxyribose, ribose or arabinose, and derivatives or analogs of 5-carbon sugars. Non-limiting examples of derivatives or analogs of 5-carbon sugars include 2'-fluoro-2'-deoxyribose or carbocyclic sugars where a carbon is substituted for the oxygen atom in the sugar ring. By way of non-limiting example, nucleosides comprising purine (i.e., A and G) or 7-deazapurine nucleobases typically covalently attach the 9 position of the purine or 7-deazapurine to the 1'-position of a 5-carbon sugar. In another non-limiting example, nucleosides comprising pyrimidine nucleobases (i.e., C, T or U) typically covalently attach the 1 position of the pyrimidine to 1'-position of a 5-carbon sugar (Kornberg and Baker, DNA Replication, 2nd Ed. (Freeman, San Francisco, 1992). However, other types of covalent attachments of a nucleobase to a nucleobase linker moiety are known in the art, and non-limiting examples are described herein.

As used herein, a "nucleotide" refers to a nucleoside further comprising a "backbone moiety" generally used for the covalent attachment of one or more nucleotides to another molecule or to each other to form one or more nucleic acids. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when the nucleotide comprises derivatives or analogs of a naturally occurring 5-carbon sugar or phosphorus moiety, and non-limiting examples are described herein.

The term "nucleic acid" encompass the terms "oligonucleotide" and "polynucleotide." The term "oligonucleotide" refers to at least one molecule of between about 3 and about 100 nucleobases in length. The term "polynucleotide" refers to at least one molecule of greater than about 100 nucleobases in length. These definitions generally refer to at least one single-stranded molecule, but in specific embodiments will also encompass at least one additional strand that is partially, substantially or fully complementary to the at least one single-stranded molecule. Thus, a nucleic acid may encompass at least one double-stranded molecule that comprises one or more complementary strand(s) or "complement(s)" of a particular sequence comprising a strand of the molecule. As used herein, a single stranded nucleic acid may be denoted by the prefix "ss", and a double stranded nucleic acid by the prefix "ds".

Nucleic acid(s) that are "complementary", "complement(s)", or "anneal" are those that are capable of base-pairing according to the standard Watson-Crick, Hoogsteen or reverse Hoogsteen binding complementarity rules. The term "complementary" refers to a nucleic acid comprising at least one sequence of consecutive nucleobases, or semiconsecutive nucleobases if one or more nucleobase moieties are not present in the molecule, are capable of hybridizing to at least one nucleic acid strand even if less than all nucleobases do not base pair with a counterpart nucleobase. Such sequences can be determined empirically by one of ordinary skill in the art. In certain embodiments, a "complementary" nucleic acid contains at least one sequence in which about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, to about 100%, and any range therein, of the nucleobase sequence is capable of base-pairing with at least one single or double stranded nucleic acid molecule during annealing.

In certain embodiments, one or more nucleic acid(s) may comprise, or be composed entirely of, at least one derivative or analog of at least one nucleobase, a nucleobase linker moiety and/or backbone moiety that may be present in a naturally occurring nucleic acid. As used herein a "derivative" refers to a chemically modified or altered form of a naturally occurring molecule, while the terms "mimic" or "analog", used herein interchangably, refers to a molecule that may or may not structurally resemble a naturally occurring molecule, but functions similarly to the naturally occurring molecule. As used herein, a "moiety" generally refers to a smaller chemical or molecular component of a larger chemical or molecular structure, and is encompassed by the term "molecule."

Nucleobase, nucleoside and nucleotide analogs or derivatives are well known in the art, and have been described in exemplary references such as, for example, Scheit, New York, 1980), incorporated herein by reference. "Purine" and "pyrimidine" nucleobases encompass naturally occurring purine and pyrimidine nucleobases and also derivatives and analogs thereof, including but not limited to, those purines and pyrimidines substituted by one or more of alkyl, caboxyalkyl, amino, hydroxyl, halogen (i.e., fluoro, chloro, bromo, or iodo), thiol, or alkylthiol wherein the alkyl group comprises of from about 1, about 2, about 3, about 4, about 5, to about 6 carbon atoms. Non-limiting examples of purines and pyrimidines include deazapurines, 2,6-diaminopurine, 5-fluorouracil, xanthine, hypoxanthine, 8-bromoguanine, 8-chloroguanine, bromothymine, 8-aminoguanine, 8-hydroxyguanine, 8-methylguanine, 8-thioguanine, azaguanines, 2-aminopurine, 5-ethylcytosine, 5-methylcyosine, 5-bromouracil, 5-ethyluracil, 5-iodouracil, 5-chlorouracil, 5-propyluracil, thiouracil, 2-methyladenine, methylthioadenine, N,N-diemethyladenine, azaadenines, 8-bromoadenine, 8-hydroxyadenine, 6-hydroxyaminopurine, 6-thiopurine, 4-(6-aminohexyl/cytosine), and the like. A table of exemplary, but not limiting, purine and pyrimidine derivatives and analogs is also provided herein below.

TABLE 1

Purine and Pyrmidine Derivatives or Analogs

| Abbr. | Modified base description |
|---|---|
| Ac4c | 4-acetylcytidine |
| Chm5u | 5-(carboxyhydroxylmethyl)uridine |
| Cm | 2'-O-methylcytidine |
| Cmnm5s2u | 5-carboxymethylaminomethyl-2-thioridine |
| Cmnm5u | 5-carboxymethylaminomethyluridine |
| D | Dihydrouridine |
| Fm | 2'-O-methylpseudouridine |
| Gal q | Beta,D-galactosylqueosine |
| Gm | 2'-O-methylguanosine |
| I | Inosine |

TABLE 1-continued

Purine and Pyrmidine Derivatives or Analogs

| Abbr. | Modified base description |
|---|---|
| I6a | N6-isopentenyladenosine |
| m1a | 1-methyladenosine |
| m1f | 1-methylpseudouridine |
| m1g | 1-methylguanosine |
| m1I | 1-methylinosine |
| m22g | 2,2-dimethylguanosine |
| m2a | 2-methyladenosine |
| m2g | 2-methylguanosine |
| m3c | 3-methylcytidine |
| m5c | 5-methylcytidine |
| m6a | N6-methyladenosine |
| m7g | 7-methylguanosine |
| Mam5u | 5-methylaminomethyluridine |
| Mam5s2u | 5-methoxyaminomethyl-2-thiouridine |
| Man q | Beta,D-mannosylqueosine |
| Mcm5s2u | 5-methoxycarbonylmethyl-2-thiouridine |
| Mcm5u | 5-methoxycarbonylmethyluridine |
| Mo5u | 5-methoxyuridine |
| Ms2i6a | 2-methylthio-N6-isopentenyladenosine |
| Ms2t6a | N-((9-beta-D-ribofuranosyl-2-methylthiopurine-6-yl)-carbamoyl)threonine |
| Mt6a | N-((9-beta-D-ribofuranosylpurine-6-yl)N-methyl-carbamoyl)threonine |
| Mv | Uridine-5-oxyacetic acid methylester |
| O5u | Uridine-5-oxyacetic acid (v) |
| Osyw | Wybutoxosine |
| P | Pseudouridine |
| Q | Queosine |
| S2c | 2-thiocytidine |
| S2t | 5-methyl-2-thiouridine |
| S2u | 2-thiouridine |
| S4u | 4-thiouridine |
| T | 5-methyluridine |
| T6a | N-((9-beta-D-ribofuranosylpurine-6-yl)carbamoyl)-threonine |
| Tm | 2'-O-methyl-5-methyluridine |
| Um | 2'-O-methyluridine |
| Yw | Wybutosine |
| X | 3-(3-amino-3-carboxypropyl)uridine, (acp3)u |

In specific embodiments, modified nucleotides may be used to confer additional properties to a nucleic acid, such as improving ease of isolation. In a non-limiting example, biotinylated dideoxynucleotides could be used for such purposes (see, e.g., U.S. Pat. No. 6,046,005, incorporated herein by reference).

In particular embodiments, it is contemplated that nucleic acids comprising one or more nucleoside or nucleotide derivatives and analogs may be used in the methods and compositions of the invention. A non-limiting example of a nucleic acid comprising such nucleoside or nucleotide derivatives and analogs is a "polyether nucleic acid", described in U.S. Pat. No. 5,908,845, incorporated herein by reference, wherein one or more nucleobases are linked to chiral carbon atoms in a polyether backbone. Another example of a nucleic acid comprising nucleoside or nucleotide derivatives or analogs is a "peptide nucleic acid", also known as a "PNA", "peptide-based nucleic acid analogs" or "PENAMs", described in U.S. Pat. Nos. 5,786,461, 5891, 625, 5,773,571, 5,766,855, 5,736,336, 5,719,262, 5,714,331, 5,539,082 and WO 92/20702, each of which is incorporated herein by reference. A peptide nucleic acid generally comprises at least one nucleobase and at least one nucleobase linker moiety that is either not a 5-carbon sugar and/or at least one backbone moiety that is not a phosphate backbone moiety. Examples of nucleobase linker moieties described for PNAs include aza nitrogen atoms, amido and/or ureido tethers (see for example, U.S. Pat. No. 5,539,082). Examples of backbone moieties described for PNAs include an aminoethylglycine, polyamide, polyethyl, polythioamide, polysulfinamide or polysulfonamide backbone moiety. In a preferred embodiment, a nucleic acid comprising one or more polyether nucleic acid or nucleoside or nucleotide derivatives and analogs may be used as a primer.

1. Primer Nucleic Acids

In many aspects of the present invention, one or more primers are annealed to one or more templates, and may be extended to produce a second complementary, or substantially complementary strand relative to the template. For a primer to be extended, it is preferred that all or part of the primer anneal to only part of the template nucleic acid.

The term "primer nucleic acid" or "primer" is meant to encompass any nucleic acid that may anneal to a template nucleic acid, thereby initiating the synthesis of a nascent nucleic acid from the end of the primer. The primer nucleic acid may be homologous to the template nucleic acid or may contain areas of homology and areas of heterology with the template nucleic acid. The term "homologous" or "homeologous" means that one single-stranded nucleic acid sequence may hybridize to another single-stranded nucleic acid sequence or its complement. The degree of hybridization may depend on a number of factors including the amount of identity between the sequences and the hybridization conditions such as temperature, salt concentration, and the concentration of other agents. The term "heterologous" means that one single-stranded nucleic acid sequence is unable to hybridize to another single-stranded nucleic acid sequence or its complement. Thus, an "area of heterology" refers to an area or a region within a nucleic acid sequence that is unable to hybridize to another nucleic acid or an area of another nucleic acid.

Primers may be provided in double-stranded or single-stranded form, although the single-stranded form is preferred. Typically, primers are oligonucleotides from about ten to about thirty base pairs in length, but longer sequences can be employed. However, a primer designed to anneal to a nucleotide sequence may be of any length. For example, a nucleotide sequence may be used to design various primers or primer sequences that can anneal to the nucleotide sequence. By assigning numeric values to a nucleotide sequence, for example, the first residue is 1, the second residue is 2, etc., an algorithm defining all primers is shown below:

$n$ to $n+y$ where n is an integer from 1 to the last number of the sequence and y is the length of the primer minus one, where n+y does not exceed the last number of the sequence. Thus, for a 10-mer, the primer correspond to bases 1 to 10, 2 to 11, 3 to 12 . . . and so on. For a 15-mer, the primer correspond to bases 1 to 15, 2 to 16, 3 to 17 . . . and so on. For a 20-mer, the primer correspond to bases 1 to 20, 2 to 21, 3 to 22 . . . and so on. Of course, a primer designed to a sequence may be less than 100% complementary to a sequence and still anneal and be useful in extension reactions, as would be known to one of ordinary skill in the art. Additionally, primers may comprise additional non-complementary sequences or non-nucleic acid molecules, such as for example biotin for isolation techniques or fluorescent compounds for detection techniques, as would be known to one of ordinary skill in the art.

The primer nucleic acid may be an RNA, a DNA, an RNA/DNA hybrid, etc. The primer may comprise one or more nucleotide or nucleoside analogues or analogs. The primer may be biologically produced, produced by the method of the invention or chemically synthesized, as would be known to those of skill in the art. In particular embodiments, a template or a primer may be isolated from at least one organelle, cell, tissue or organism. Methods for isolating nucleic acids from biological sources are well known to those of skill in the art (see Sambrook et al., 1989). In certain embodiments, the primer is a synthetic oligonucleotide. Oligonucleotide synthesis is well known to those of skill in the art. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A primer that selectively hybridizes to nucleic acids corresponding to a desired sequence (e.g., a gene) is contacted with the isolated nucleic acid under conditions that permit selective hybridization. It is contemplated that the primer nucleic acid may anneal to the template nucleic acid within a region that is part of or outside of an encoding sequence, such as for example a gene or a gene family, within an intergenic region of a group of genes, or outside of a gene. If the invention is applied to gene recombination it is contemplated that a common primer-annealing region may be attached to all the individual template nucleic acids.

A number of modifications or features may be part of the primer nucleic acid. It may be desirable to include, 5' of the annealing region on the primer nucleic acid, additional nucleotides that facilitate transcription, translation, purification of a peptide, polypeptide or protein that may be encoded by the nascent nucleic acid, immobilization of the peptide, polypeptide or protein, or combinations of these modifications and/or features.

In particular embodiments it is contemplated that the primer nucleic acid may also contain internal modifications. Such modifications may include but are not limited to phosphorothioate linkages between nucleotides and non-nucleotide insertions such as carbon chains, as described herein.

Excess primer nucleic acid may be removed from the mixture after the first round of extension or at anytime during the method of the invention. Those skilled in the art will be aware of methods for removing primer nucleic acid (Sambrook et al., 1989).

2. Template Nucleic Acid

The term "template nucleic acid" means a nucleic acid that may anneal to a primer nucleic acid and serve as the template for nucleic acid synthesis. Nucleic acid used as a template for nucleic acid synthesis or amplification may be isolated from cells contained in a biological sample, according to standard methodologies (Sambrook et al., 1989). The nucleic acid may be genomic DNA or fractionated or whole cell RNA. Where RNA is used, it may be desired to convert the RNA to a complementary DNA. In one embodiment, the RNA is whole cell RNA and is used directly as the template for amplification or extension.

The template nucleic acid may be, for example, DNA, RNA, DNA/RNA hybrids, or any composition of nucleic acids that can be copied with a polymerase and may be isolated from biological sources or synthetically prepared. The template nucleic acid may be any length that allows for annealing and extension of the primer nucleotide. The template nucleic acid may be isolated from any source including bacteria, yeast, viruses, and higher organisms or isolated from any fraction of these sources. Template nucleic acid may be prepared by PCR™ or may be present in a vector and used after excision from a vector. It is also contemplated that complete vectors containing the template nucleic acid may be used in this invention.

The nucleotide and protein, polypeptide and peptide sequences for various genes have been previously disclosed. In certain embodiments, the template or primer sequence may be obtained from a public source, such as, for example, a computerized database known to those of ordinary skill in the art. One such database is the National Center for Biotechnology Information's Genbank and GenPept databases. The coding regions for these known genes may be amplified and/or expressed using the techniques disclosed herein or by any technique that would be know to those of ordinary skill in the art. In certain embodiments, the primer may be a degenerate primer designed based on a peptide sequence, as would be known to one of ordinary skill in the art.

Preferably the starting form of the template nucleic acid will be single-stranded. Single stranded template may be isolated in circular form within a vector, such as, for example, from a M13 type bacteriophage (Messing & Vieira, 1982) or another bacteriophage that packages single-stranded nucleic acid. Alternatively, single-stranded template nucleic acid may be prepared from purified double-stranded nucleic acid by any number of methods known to those skilled in the art. Such methods include but are not limited to asymmetric degradation of the non-template strand and linear PCR™. Alternatively, a double-stranded plasmid DNA may be denatured by methods known to those skilled in the art. If it is desired that a nucleic acid of interest is free of vector sequence(s), other methods for obtaining a single-stranded template nucleic acid may be used by someone skilled in the art. These include, but are not limited to, asymmetric PCR™, asymmetric digestion of a double-stranded linear template nucleic acid (i.e., digesting one strand of a double-stranded nucleic acid with an exonuclease), in vitro transcription, chemical synthesis, etc. It is also contemplated that single stranded RNA can be used as template and may be prepared by in vitro transcription.

If a template nucleic acid is linear it will be preferable, in some embodiments, that the 3' end of a template nucleic acid be resistant to exonucleolytic degradation. The term "exonucleolytic" means degradation of a nucleic acid from the ends of the polymer. Some exonucleases degrade nucleic acids from the 5' end, some from the 3' end, and some from both 5' and 3' ends simultaneously. A method for blocking one strand of a double-stranded nucleic acid to exonucleolytic degradation by Exonuclease III can be found in U.S. Pat. No. 4,521,509, incorporated herein by reference. The term "blocking exonucleolytic degradation" means preventing exonucleolytic removal of a terminal nucleotide or nucleotides in a nucleic acid. Without being limited by the examples, it is contemplated that methods for blocking exonucleolytic degradation may employ the ligation of one or more oligonucleotides comprising at least one blocking group to the 3' terminus of a template nucleic acid. A blocking group may include but are not limited to a peptide nucleic acid (PNA), a dye, a "carbon spacer" (e.g., C18, C3), an "amino modifier C7", a "C3 thiol modifier", a Dabcyl, an invert base, a long glycol chain, or a deoxyribonucleotide 5'-O-[1-thio] triphosphate (FIG. 4).

Double-stranded or partly double stranded nucleic acid template may be utilized in the invention. The double-stranded nucleic acid should be denatured or partly denatured to allow for annealing of the primer nucleotide. Denaturation of double-stranded nucleic acid can be performed by a variety of methods known to those skilled in the art.

Template nucleic acids or nucleic acid extension ladders (described herein below) derived from one or more templates may be added to the mixture before, during, or after any step of the invention.

3. Template Pools

Template nucleic acid may be prepared as part of the invention and be derived from a process of bi-directional extension as described in a following section. Recombined nucleic acids of interest that are produced by the method of the invention may be used as templates in subsequent rounds of recombination in this invention. In this manner, even more desirable nucleic acids may be recovered. Additional rounds of recombination may also include the presence of different wild-type templates, mutant templates or combinations thereof. Rounds of recombination with wild-type nucleic acid template and a subpopulation of recombined nucleic acids from a first or subsequent round of recombination may be conducted so as to remove any silent mutations from the subpopulation.

Nucleic acid recombination can be performed on a pool of nucleic acids that are substantially related in sequence or on a pool of nucleic acid sequences with one or more areas or small areas of identity. The term "related nucleic acid", "nucleic acids that are related", "sequences that are related" and "related sequences" means that a region or an area of the nucleic acids are identical and a region or area of the nucleic acids are heterologous. Thus, the term "minimally related" means that nucleic acids have one or a few areas or a small area(s) of identity and many or large areas of heterology. The term "identical" or "identity" means that two nucleic acid sequences have the same sequence or complementary sequence. Thus, "area of identity" means that a region or area of a nucleic acid is identical or complementary to another nucleic acid. An "area of identity" may comprise a single nucleotide, but more often an "area of identity" is meant to comprise two or more nucleotides, and more preferably four or more nucleotides.

A pool of related sequences with mutations may be used and may be created by a number of methods, including error-prone PCR™, oligonucleotide-directed mutagenesis, chemical mutagenesis, the method of the invention or other methods known in the art.

The nucleic acid recombination method of the invention can be performed on a pool of nucleic acids with unknown sequences. It is contemplated that the nucleic acid recombination may be conducted with nucleic acids from a subpopulation of a population.

Enrichment or purification of the pool of reassembled or recombined nucleic acids may facilitate subsequent manipulations of this nucleic acid pool. The term "reassembled nucleic acid" or "nucleic acid reassembly" is used when recombination occurs between identical sequences. By contrast, the term "recombined nucleic acid" or "nucleic acid recombination" is used when recombination occurs between non-identical sequences. Several methods known to those skilled in the art may be used for enrichment or purification of reassembled or recombined nucleic acids. The pool of recombined nucleic acids may be enriched by PCR™ amplification using primers that are specific for sequences on the ends of or flanking the recombined nucleic acids. The term "amplification" or "amplified" means that the number of copies of a nucleic acid is increased.

By another example, it may be desirable to use a template nucleic acid in a form that facilitates its removal after the reassembly or recombination reaction. For example, one method for producing a template nucleic acid in such a form uses a polymerase chain reaction in which dTTP has been replaced with dUTP. Templates so produced will have dUTP incorporated throughout their length. After performing the reassembly or recombination method of this invention using such templates, the mixture is incubated with Uracil N-Glycosylase (UNG) which will cleave the nucleic acid template at UMPs. As used herein, the term "cleave" or "cleaving" means breaking, (e.g., a nucleic acid) by enzymatic or other means. Complete degradation of the abasic polynucleotide with heat treatment results in the elimination of the template nucleic acids. This method has been successfully used for "PCR Carry-over Prevention" (Longo et al., 1990). The extension ladder products will be protected from the activity of UNG because they will have been synthesized with dTTP, not dUTP.

Other methods for enriching or purifying the reassembled or recombined nucleic acids are discussed herein.

B. Primer Extension

For the initiation of nucleic acid synthesis and production of a nucleic acid, a primer nucleic acid is annealed to a template nucleic acid. The primer is extended to produce an "extended nucleic acid." However, the primer and/or the primer sequence may or may not comprise the extended nucleic acid. For example, in certain embodiments the primer may be degraded or removed by cleavage.

A primer nucleic acid may be designed to specifically anneal anywhere along a template nucleic acid. For the production of a chimeric nucleic acid, it may be desirable to use a template nucleic acid that comprises at least one gene or other encoded sequence and to use a primer nucleic acid that anneals near the 3' end of each of one or more template strand(s). The term "chimeric nucleic acid" means that the nucleic acid sequence comprises regions from two or more nucleic acids that do not have the same sequence. Alternatively, a common primer-annealing region can be engineered to be present 3' of the coding region of each of one or more template strand(s) that will be used in the recombination method.

Figure 2:
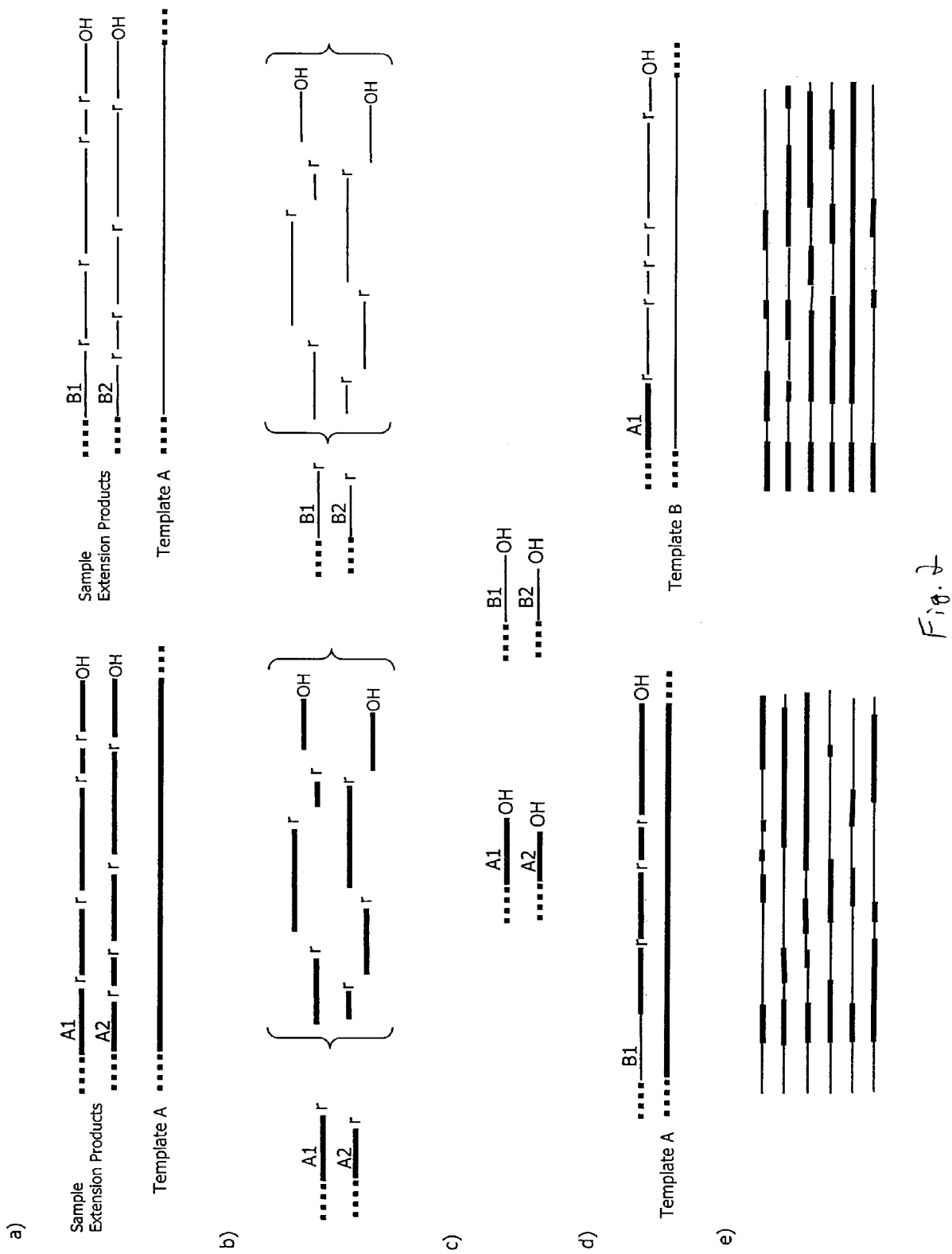
FIGS. 2A, 2B, 2C, 2D and 2E Selected steps involved in the synthesis of nucleic acid sequences.

Polymerization of a nascent nucleic acid from the 3' end of a primer nucleic acid can be achieved by numerous methods. Typically, an annealed primer nucleic acid and a template nucleic acid are incubated with a nucleic acid polymerase, dNTPs (e.g., dATP, dCTP, dGTP, and dTTP, FIG. 4), and any additional agent(s) for the particular polymerization reaction under conditions that allow for nucleic acid synthesis. The polymerase may be, for example, the Klenow fragment, Taq polymerase, T7 DNA polymerase or any other nucleic acid polymerase known in the art. The use of a heat-stable polymerase or a modified polymerase (e.g., Thermosequenase or Sequenase) may be desirable in certain embodiments. In certain aspects, it may be preferred that all steps in the invention proceed to equilibrium or plateau. In a preferred embodiment, a chain-terminating agent, such as for example, at least one ddNTP (e.g., ddATP, ddCTP, ddGTP, ddTTP; FIG. 2) are included in the incubation mixture, as described below.

1. Length-Altering Agents

In preferred aspects, the methods and compositions of the invention comprise a length-altering agent. The term "length-altering agent" means an agent that may either terminate chain-elongation or be used to later shorten an extended nucleic acid (e.g., a chemical agent). In specific aspects, the length-altering agent may comprise a nucleotide, a modified nucleotide or a nucleotide analog. In particular aspects, the length-altering agent is incorporated into a nucleotide chain during nucleic acid synthesis. In certain embodiments it is incorporated enzymatically. In further aspects, the length-altering agent terminates chain-elongation upon incorporation into an elongated chain. As used herein, a length-altering agent that terminates chain-elongation is referred to as a "chain-terminating agent."

In certain embodiments, for example, it is contemplated that any compound described herein or known to one of skill in the art that can be incorporated into a growing nucleotide chain resulting in the termination of chain elongation, and/or that can be a site of cleavage or a site for removal of a subunit (e.g., a nucleotide, a modified nucleotide, a nucleotide analog) or be a site for modification (e.g., chemical or enzymatic modification) may be used as a length-altering agent. It is contemplated that any compound that can be incorporated into a growing polypeptide chain resulting in the termination of chain elongation and that can then be removed or modified, thereby regenerating a 3' OH terminus from which nucleic acid extension can begin, may be used as a chain-terminator in the invention. The compound may be removed or modified by enzymatic (e.g., Exonuclease III as described in the Examples, the exonucleolytic activity of $T_4$DNA polymerase (Barcak and Wolf, 1986), the exonucleolytic activity of the Klenow fragment of E. coli DNA polymerase I (Sambrook et al., 1989) chemical, light (Fodor et al., 1991), or thermal methods. Similarly, the compound may be removed and replaced with an exchange reaction. In other facets, the length-altering agent may comprise a treatment of an extended nucleic acid to alter its length, such as for example, enzymatic or chemical cleavage of an extended nucleic acid. In particular facets, the length-altering agent may inhibit further extension of an extended nucleic acid. In specific aspects, part or all of a length-altering agent present in an extended nucleic acid or in a reaction mixture comprising an extended nucleic acid may be removed. In further aspects, the length-altering agent may be removed before an additional manipulation of an extended nucleic acid, such as, for example, further extension of an extended nucleic acid. Various types and uses of length-altering agents are described herein, however, one of skill in the art may adapt length-altering agents in the method and compositions of the invention beyond the examples described herein without departing from the spirit and scope of the present invention.

2. Nucleic Acid Extension Ladder

In the preferred embodiment, incubation of the mixture results in the synthesis of a nucleic acid extension ladder (FIG. 1). A nucleic acid extension ladder may be produced by including or adding a length-altering agent (e.g., a dideoxyribonucleotide) during nucleic acid synthesis.

For example, a length-altering agent can be incorporated into a nascent nucleic acid, thereby terminating extension of a nucleotide chain. In another embodiment, a "nucleic acid extension ladder" may also be produced by chemically or enzymatically treating a double-stranded nucleic acid mixture in such a way that results in the production of partially double-stranded nucleic acids. In a preferred embodiment the length of the single stranded nucleic acids vary by single nucleotide increments. However, members of a "nucleic acid extension ladder" may differ in length by more than one nucleotide increments, depending on the types of length-altering agents used, the ratios of agents, the reaction conditions, etc. Their lengths may range from a length equal to that of the primer plus one nucleotide to a length equal to that of the template nucleic acid (including the primer).

After a round of extension, the result is a pool of partially double-stranded nucleic acids that may also include a completely double-stranded nucleic acid. A double stranded nucleic acid in this aspect of the invention will comprise the template as one strand and members of the newly synthesized nucleic acid as the other strand.

In a preferred aspect, a nucleic acid extension ladder can be used for the synthesis of mutant or chimeric nucleic acids. In general any method may be used which creates an extension ladder, whereby an incorporated component (e.g., modified or unmodified nucleotides) that includes the scissile link is removed prior to subsequent cycles of annealing and extension, described below.

It is another important aspect of the invention that primarily only those extension ladder products, which are derived from extension of a primer sequence, participate in the recombinatorial process. That is to say, any randomly generated fragments, such as may be produced by other methods used to generate an extension ladder, will not substantially contribute to the final pool of recombined nucleic acids.

Figure 3:
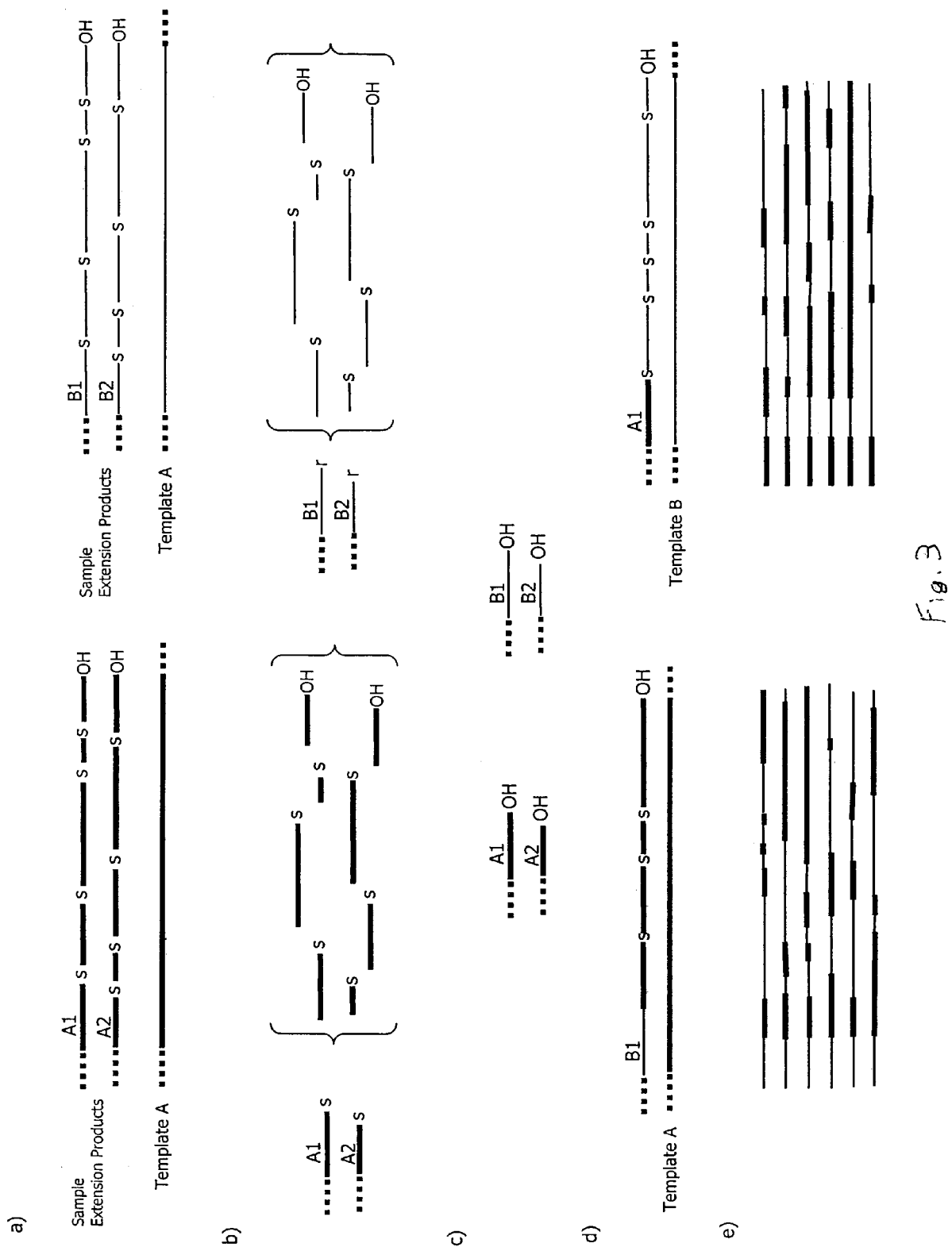
FIGS. 3A, 3B, 3C, 3D and 3E Selected steps involved in the synthesis of nucleic acid sequences.

Nonetheless, in less preferred embodiments, alternative procedures may be used to create a nucleic acid extension ladder. Some of these may generate a ladder whose members do not all possess defined 5' ends (FIG. 2, FIG. 3). That is, one or more additional nucleic acid fragments may be produced that are of random size and distributed throughout the length of the newly synthesized nucleic acid chains. For example, production of a nucleic acid extension ladder may be achieved through the incorporation of deoxyribonucleotide [1-thio] triphosphates (dATP-alpha-S, dCTP-alpha-S, dGTP-alpha-S, dTTP-alpha-S; Amersham) followed by specific alkylation and cleavage at the phosphorothioate bonds (Gish & Eckstein, 1987). Another alternative for the production of nucleic acid extension ladders utilizes chemical cleavage and the methods described by Maxam and Gilbert (Maxam & Gilbert, 1980). Briefly, separate chemical reactions allow cleavage at naturally occurring nucleotides (Sambrook et al., 1989). Variations of the Maxam and Gilbert chemical cleavage method are also contemplated (Ambrose and Pless, 1987).

Yet another alternative method for the generation of an extension ladder (FIG. 2) employs the random incorporation of one or more ribonucleotide (e.g., ATP, CTP, GTP, UTP, a ribonucleotide derivative, a ribonucleotide analog, or a combination thereof), along with one or more deoxyribonucleotides (e.g., an dATP, a dCTP, a dGTP and/or a dTTP) during an extension step. This creates scissile links in a nascent nucleic acid wherever a ribonucleotide is positioned. Therefore, a newly synthesized nucleic acid can be cleaved, for example, with either alkaline hydrolysis or with a ribonuclease, thereby creating a nucleic acid extension ladder. Optional alkaline phosphatase treatment followed by an Exonuclease III treatment may remove a terminal ribonucleotide base from one or more members of a newly created extension ladder, leaving a 3' OH for the next cycle of extension and/or recombination.

An unknown sequence as well as a known sequence can participate in the recombination as long as a specific primer-binding site is known or added to a site flanking a region for recombination. If it is desired, a region within a nucleic acid may be easily targeted for recombination, and any region may be targeted by orienting an initial extension primer at or near a 3' end of the desired region on a template nucleic acid. Regions may be targeted by altering the dNTP:ddNTP ratios, by including only one, two, three, or all four ddNTPs, by including one, two, three, or all four α-phosphorothioate dNTPs, or various combinations of the above nucleotides or other nucleotide analogs or derivatives. This effectively alters the bias and frequency of sizes of one or more nucleic acids during extension and the 3' terminal nucleotide of each member.

It is contemplated that a random-sized and a randomly distributed fragment generated by the alternative embodiments may be used with other methods for recombinatorial nucleic acid synthesis or "gene shuffling" methods (Stemmer, 1994; Zhao et al., 1998). The terms "recombinatorial nucleic acid synthesis", "gene shuffling", "nucleic acid shuffling" or "DNA shuffling" are used to indicate a particular method or family of methods that mediate recombination between non-identical nucleic acid sequences. In nucleic acid shuffling, mixtures of related nucleic acid sequences or polynucleotides are randomly fragmented and reassembled to yield a library or mixed population of recombinant nucleic acid molecules or polynucleotides.

3. Removal of a Length-Altering Agent

In one embodiment, a nucleic acid mixture is further incubated under conditions that result in removal of a length-altering agent (e.g., a ddNMP) from one or more terminated nucleotide chains, thereby generating an extendable 3' terminus from which nucleic acid synthesis can begin in the next cycle. A synthesized nucleic acid extended from an oligonucleotide primer in the previous extension will be available in the subsequent steps. It is expected that there will be little or no interfering or non-productive fragments generated, and all or virtually all fragments will have 5' sequences defined by an initiating oligonucleotide. In a particular embodiment, a primer extension product may be used for in vitro recombination, as described herein.

Preferred methods for generating extension ladders are those which generate a pool of members with defined 5' ends and staggered, terminated ends, such that the lengths of the members preferably differ by a single nucleotide (FIG. 1). For example, the use of length-altering nucleotides (e.g., dideoxynucleotides) as described as a preferred embodiment is one such method. Another preferred method utilizes exonucleolytic cleavage of nascent nucleic acids containing randomly incorporated deoxynucleoside [1-thio] triphosphates (Labeit et al., 1986). In this method dNMPs will be excised from the 3' end of a nucleic acid by an exonuclease (e.g., Exonuclease III) and degradation will stop at the incorporated deoxynucleoside [1-thio] triphosphates. Both of these approaches will produce a preferred, defined nucleic acid extension ladder without creating potentially inhibitory, non-defined fragments.

a. Exonuclease III

As described in Example 1, Exonuclease III is one such enzyme that may remove a terminal ddNMP from a nucleic acid. Exonuclease III is active with double-stranded nucleic acids that possess a recessed 3' end on the strand being degraded. In contrast to what has been reported (Eun, H-M., 1996; U.S. Pat. No. 4,521,509), the inventors have found that Exonuclease III may cleave a terminal dideoxynucleotide from a recessed 3' end of a double-stranded nucleic acid. That is, exonucleolytic activity is not dependent on the presence of a terminal 3' OH group.

b. Other Exonucleases

Other exonucleases (Skalski et al., 1995) may remove a 3' terminal ddNMP. It is contemplated that other enzymes, such as polymerases, whose primary activity is not exonucleolytic may also function to remove a terminal dideoxynucleotide.

c. Inhibition of Exonucleolytic Activity

During or after incubation and removal of the length-altering agent (e.g., a ddNMP), the exonucleolytic activity is inhibited or inactivated. In one embodiment it will be desirable to limit the exonucleolytic cleavage to remove only the terminal ddNMP with an exonuclease (e.g., Exonuclease III), so that exonucleolytic activity can be inhibited or inactivated by one of several means, before the newly synthesized strands are completely degraded. One skilled in the art may employ several methods for inhibiting or inactivating exonucleolytic activity (Sambrook et al., 1989). Some of these methods include, for example, limiting the time for exonucleolytic degradation, lowering the temperature, adding agents (e.g., NaCl) to the mixture, and using less enzyme in the mixture (Example 2). Any method that limits exonucleolytic degradation may be used. One particularly advantageous approach is to limit the exonucleolytic removal of nucleotide to the terminal ddNMP or to the terminal ddNMP and as few dNMPs as can be achieved.

In certain aspects, the exonuclease activity will be inactivated after removal of the length-altering agent. For example, Exonuclease III can be inactivated by heat. Other methods of inactivating exonucleases and exonucleolytic activity will be apparent to those skilled in the art (Sambrook et al., 1989).

In a preferred embodiment, it will be desirable to remove the ddNMP from the terminated nucleotide chains while preventing further degradation of the nucleotide chain from the 3' end. A particularly advantageous method for inhibiting exonucleolytic activity after the removal of the terminal ddNMP is to use deoxyribonucleotide [1-thio] triphosphates, (FIG. 4) in place of dNTPs during the synthesis step (Example 3). The phosphorothioate bond thus generated between adjacent nucleotides will be blocked to exonucleolytic activity (e.g., Exonuclease III activity), thereby allowing for exonucleolytic cleavage of the terminal ddNTP from members of the nucleic acid extension ladder and inhibiting further exonucleolytic degradation of the newly synthesized nucleic acid strands.

4. Denaturation of a Primer-Extended Strand/Template Strand

In a preferred embodiment, after removal of the 3' ddNMP and inactivation of the exonuclease activity, the pool of nucleic acids (a defined nucleic acid extension ladder and template nucleic acid(s)) is denatured, such as, for example, by heating. One skilled in the art can determine the appropriate conditions for complete denaturation of double-stranded nucleic acid. Preferably, the temperature is from about 80° C. to about 100° C., more preferably the temperature is from about 90° C. to about 96° C. Lower temperatures may be used for denaturation if agents are added that are known to enhance denaturation (e.g., glycerol, betaine, proline, and DMSO among others). Other methods in the art may be used to denature the nucleic acids, including pH and pressure.

5. Annealing the Primer-Extended Strand to a Template Strand

Following denaturation, the nucleic acid extension ladder and template(s) are annealed. Annealing may be promoted, for example, by cooling. Preferably, the temperature is from about 4° C. to about 75° C., more preferably the temperature is from about 35° C. to about 70° C. One skilled in the art may use methods to affect the annealing of complementary or partially complementary nucleic acids. Such methods may include, for example, the addition of salts (e.g., NaCl, KCl), polyethylene glycols, dextran sulfate, betaine, proline, tetramethylammonium chloride, or others that would be known to one of ordinary skill in the art.

The template to which an individual primer-extended strand may anneal may comprise the same or different sequences as the template from which it was denatured. If the template to which a primer extended strand is different in sequence from the template from which the primer extended strand was denatured, then further extension of the primer extended strand with the new template may result in a mutation or chimerization of the primer extended strand relative to the sequence of the template strand from which it was extended and denatured. Use of templates that vary in sequence from one extension reaction to another extension reaction (i.e., extension "cycles"), will promote nucleic acid or gene recombination of the sequences of the templates in the sequence of the primer extended strand. The creation of a nucleic acid extension ladder followed by cycles of regenerating an extendable 3' terminus, denaturation, re-annealing, and incubation with polymerase, is referred to herein as nucleic acid reassembly or recombinatorial nucleic acid synthesis.

If the method of nucleic acid or gene recombination is being employed, it may be desirable to increase the frequency of recombination among template nucleic acids by using a lower annealing temperature such as a temperature substantially below or at the $T_m$ of the annealing region. An annealing region may be as small as one nucleotide. It is contemplated that this approach may also be used to increase the rate of mutation if a single template nucleic acid is used, as in the method of nucleic acid reassembly.

6. Multiple Extension Cycles

An important aspect of this invention is that members of the nucleic acid extension ladder anneal to template nucleic acids and act as primers in the cycles of nucleic acid reassembly or recombinatorial nucleic acid synthesis to generate another nucleic acid extension ladder in each cycle. Nucleic acids in the extension ladder pool can serve as extendable substrates for each successive cycle of synthesis/recombination. Therefore, it is contemplated that as more cycles are performed the length of each member of the nucleic acid extension ladder will increase. The cycle is repeated for the desired number of times. In certain embodiments, the cycle is repeated preferably about 2 to about 100 times.

Typically, the newly annealed nucleic acid extension ladder and templates are incubated with nucleic acid polymerase, dNTPs or α-phosphorothioate dNTPs, and a length-altering agent is included or added (e.g., ddNTPs) under conditions that allow for nucleic acid synthesis. If denaturation renders the polymerase inactive, it will be necessary to add active polymerase for the next round of nucleic acid synthesis. Polymerase may be added to the mixture prior to annealing, simultaneously with annealing, or after annealing.

Following the final cycle of reassembly or recombination, an additional cycle may be performed and excess dNTPs or α-phosphorothioate dNTPs are included in the polymerase incubation step. Prior to this cycle it may be desirable to remove any remaining ddNTPs or other length-altering agents from the incubation mixture. Incubation with polymerase in the presence of excess dNTPs will extend all the nascent nucleic acids, that is all members of the nucleic acid extension ladder, to the end of the template nucleic acid.

7. Mutation of Extension Products

The invention is suitable for random mutagenesis or for targeting a region of a nucleic acid for mutagenesis. Not being limited by the following examples, any number of methods may be applied to increase the mutation frequency during a polymerase extension step.

For example, if it is desirable to mutate or recombine only a portion of a nucleic acid, a primer nucleotide can be designed to specifically anneal anywhere along a nucleic acid. Varying the amounts of nucleotides and length-altering agents may have the effect of targeting a certain region of a template nucleic acid for mutagenesis or recombination. Increasing the dNTP:ddNTP ratio in an extension reaction will promote the synthesis of a nascent chain-terminated nucleic acid with a longer average chain length. Decreasing the dNTP:ddNTP ratio will promote the synthesis of a nascent chain-terminated nucleic acid with a shorter average chain length. These modifications may serve to decrease or increase, respectively, the mutation frequency. To achieve variations in chain length, the ranges of dNTP:ddNTP ratios can be altered. For example, with Thermosequenase a 100:1 ratio used in the precise reaction conditions described in manufacturer's instructions (U.S. Biochemical) will typically give a large range of lengths (up to about 600 bases) among nascent chain-terminated nucleic acids. Going to a 150:1 ratio will give longer lengths, going to a 50:1 ration will give shorter lengths. The precise ratio for each reaction would be determined empirically as would be within the skill of one in the art in light of the present disclosures.

In some embodiments, it is contemplated that insertions or deletions of nucleotides, or both may occur during the method of the invention and may be enhanced under conditions of relaxed annealing stringency.

In certain embodiments, it may be desirable to alter the number of cycles in the method of the invention so as to target a certain region of a nucleic acid template for mutagenesis or recombination. By example, a limited number of cycles (e.g., about 2 to about 10) of the invention may be performed with a low ratio of dNTPs:ddNTPs followed by a final cycle with excess dNTPs to make nucleic acids completely double-stranded. This would have the effect of increasing mutagenesis or recombination nearer to a primer nucleic acid.

In some embodiments dITP may be added to the polymerase extension, either in place of one or more dNTPs or in addition to dNTPs. A mutation may also be introduced into a nascent nucleic acid by altering the conditions of a polymerase extension step, thereby reducing the fidelity of the polymerase.

In an embodiment of the invention, both strands of a double-stranded nucleic acid may be used as a template for the generation of an extension ladder by a process of bi-directional extension ladder synthesis. As an example, one strand of a nucleic acid may serve as one template and the other strand may serve as another template. Identical or different primer annealing sites may be present at the 3' end of each template for initiating polymerase extension. In this mixture, polymerase extension in the preferred length-altering embodiment will generate two nucleic acid extension ladders, one from each homologous template nucleic acid. The extension ladders will contain regions of overlapping sequence complementarity. When the extension ladders are converted to extendable primers themselves, they are free to anneal with the complementary and overlapping nucleic acids from the homologous extension ladder and use the nucleic acids as template in the next cycle of extension and termination. Alternatively or additionally, the homologous original template nucleic acids may function as template in subsequent cycles. This aspect of bi-directional extension recombination may result in an increased usage of mutated nucleic acid extension ladder as template, thereby increasing the complexity of the final recombined nucleic acid pool.

In another embodiment of the invention, it may be desirable to use modified nucleotides or nucleotide analogs during polymerase extension. A mixture of α-phosphorothioate dNTPs, dNTPs, and ddNTPs may be used in the nucleic acid extension. If an exonuclease is subsequently used in the cleavage step, this may result in removal of more nucleotides than only the 3' length-altering nucleotide, thereby increasing the complexity of the nucleic acid extension ladder.

When the method of the invention uses ddNTPs as a length-altering agent (as in a preferred embodiment) or another length-altering agent that interacts with specific complementary nucleotides, it may be desirable to include a subset of the length-altering agent. In a non-limiting example, a polymerase extension may include four dNTPs and two ddNTPs. This would have the effect of creating a nucleic acid extension ladder that is precisely defined but not terminated at every possible nucleotide, thereby reducing the complexity of the nascent nucleic acid extension ladder.

8. Other Manipulations

It may be desirable to capture or purify an extendable fragment. This can be done using well-established methods, including but not limited to biotin capture, either magnetic or antibody based. For example, dideoxynucleotides contain a biotin moiety (e.g., attached to the nucleotide by a photocleavable link; see U.S. Pat. No. 6,046,005 incorporated herein by reference) may be used to enhance the ease of purification of terminated products. This purification could take place after the first round or after each round of extension. The dideoxynucleotide and hence the attached biotin moiety would be removed by exonuclease during the regeneration of an extendable terminus for the next round.

In certain embodiments, such as for example, preparation for cloning, it may be desirable to make the newly synthesized nucleic acids double-stranded. Single-stranded recombined or reassembled nucleic acids will be present in the mixture along with single-stranded or double-stranded template nucleic acids. It will be useful to first isolate and/or purify the nascent nucleic acids from the polymerase extension mix containing the template nucleic acid. This step may be simplified if the original primer nucleic acid was modified in a manner that facilitates purification or isolation of newly synthesized nucleic acids. Such modifications will be known to one skilled in the art and may include 5' biotinylation, but are not limited to that example. Nucleic acids may be made double-stranded by annealing a primer to a region of the nascent nucleic acid that is 3' of the region that was recombined or mutagenized and incubating the mixture with a polymerase and dNTPs under conditions that allow for nucleic acid synthesis. The primer-annealing region may be present in the vector that carried the template nucleic acids or at or near the 3' end of the recombined or mutagenized portion of the nucleic acid.

An extended, reassembled or recombined nucleic acid may be stored, preferably below about 4° C., or used at any time.

C. Products of Recombinatorial Nucleic Acid Synthesis

One or more mutated or synthesized nucleic acids of the present invention may encode for a peptide or polypeptide, or a transcribed nucleic acid. All such compositions are encompassed by the present invention. Altered nucleic acids and/or encoded peptides or polypeptides produced by the methods of the present invention may have various uses, as would be known to one of ordinary skill in the art and described herein. For example, a nucleic acid mutated or created by the methods described herein may encode a peptide or polypeptide that has new or altered properties. Other non-limiting examples are described below.

1. Aptamers

The methods of the present invention may produce nucleic acids with unique or improved binding characteristics to a target molecule. Thus, in certain embodiments, a nucleic acid, particularly an extended nucleic acid, may comprise or encode an aptamer. An "aptamer" as used herein refers to a nucleic acid that binds a target molecule through interactions and/or conformations other than those of nucleic acid annealing/hybridization described herein. Methods for making and modifying aptamers, and assaying the binding of an aptamer to a target molecule may be assayed or screened for by any mechanism known to those of skill in the art (see for example, U.S. Pat. Nos. 5,840,867, 5,792,613, 5,780,610, 5,756,291 and 5,582,981, incorporated herein by reference). In certain embodiments, the aptamer is an RNA molecule. RNA aptamers are known in the art, and may bind various small molecules, such as for example fluorophores (see, e.g., Holeman et al., 1998). In certain embodiments, the aptamer (e.g., DNA or RNA) may possess a catalytic activity, such as the ability to cleave another molecule such as for example, a nucleic acid.

2. Ribozymes

In certain embodiments, the extended nucleic acid sequence may express RNAs that are not translated. DNA may be introduced into organisms for the purpose of expressing RNA transcripts that function to affect phenotype yet are not translated into protein. However, as detailed below, DNA need not be expressed to effect the phenotype of an organism.

The RNA may possess various activities or functions. A non-limiting example is an RNA with ribozyme activity. A ribozyme may serve possible functions in reducing or eliminating expression of native or introduced genes. Other functions for ribozymes are known in the art, such as, for example, tRNA aminoacylation, 5'—5' ligase activity, AMP-activated RNA substrate ligation, RNA replication and protein synthesis, amino-acid transfer reactions, polynucleotide kinase activity and self-alkylation (see references such as Lee et al., 2000; Holeman et al., 1998; Chapman and Szostak, 1995; Hager. and Szostak, 1997; Hager et al., 1996; Lohse and Szostak, 1996; Lorsch and Szostak, 1995; Wilson and Szostak, 1995; and Breaker and Joyce,. 1995, each incorporated herein by reference). It is contemplated that one of ordinary skill in the art can produce and isolate ribozymes with these and other activities by the methods of the present invention, in light of the disclosures herein.

Nucleic acids may be constructed or isolated which, when transcribed, produce RNA enzymes (ribozymes) that can act, for example, as endoribonucleases and catalyze the cleavage of RNA molecules with selected sequences. In a particular aspect of the invention, nucleic acids may be mutated to produce a ribozyme with an altered property, such as, for example, activity or specificity.

Designing and testing ribozymes for efficient cleavage of a target RNA is a process well known to those skilled in the art. Examples of scientific methods for designing and testing ribozymes are described by Chowrira et al., (1994) and Lieber and Strauss (1995), each incorporated by reference. In the present invention, it is contemplated that one or more regions, such as for example, a catalytic region, of a known ribozyme may be mutated or chimerized to produce a ribozyme with an altered activity. The identification of operative and preferred sequences for use in down regulating a given gene is simply a matter of preparing and testing a given sequence, and is a routinely practiced "screening" method known to those of skill in the art.

D. Cloning Extension Products

It may be desirable to clone the recombined or reassembled nucleic acids into an appropriate vector and transform the ligation mixture into a viable cell (e.g., bacteria, yeast, fungi, or other eukaryotic cell).

1. Vectors

The vector used for cloning is not critical provided that it will accept a nucleic acid fragment of the desired size. If it is desired to express peptides that may be encoded by the cloned nucleic acid fragment, the vector should comprise signals for transcription and translation next to the site of insertion of the nucleic acid fragment, to allow for expression in the host cell. The signals may be part of the inserted nucleic acid fragment. Signals that enhance transcription of the cloned nucleic acid fragment may also be present in the vector. The vector may also comprise signals or features that facilitate or enhance expression, isolation, purification, or secretion of a peptide that may be encoded by the nucleic acid fragment.

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Maniatis et al., 1988 and Ausubel et al., 1996, both incorporated herein by reference.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

a. Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. No. 4,683,202, U.S. Pat. No. 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the polypeptide, peptide or transcript encoded by a nucleic acid (e.g., a DNA segment) in the cell type, organelle, and organism chosen for expression. Those of skill in the art of molecular biology generally know the use of promoters, enhancers, and cell type combinations for protein expression (for example, see Sambrook et al., 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

b. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

C. Multiple Cloning Sites

Vectors can include a multiple cloning site (MCS), which is a nucleic acid region that contains multiple restriction enzyme sites, any of which can be used in conjunction with standard recombinant technology to digest the vector. (See Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

d. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression. (See Chandler et al., 1997, herein incorporated by reference.)

e. Termination Signals

The vectors or constructs of the present invention may comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to be more stable and are translated more efficiently. Thus, in other embodiments involving eukaryotes, it is preferred that the terminator comprises a signal for the cleavage of the RNA, and it is more preferred that the terminator signal promotes polyadenylation of the message. The terminator and/or polyadenylation site elements can serve to enhance message levels and/or to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

f. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, or any polyadenylation signal convenient and/or known to function well in various target cells. Polyadenylation may increase the stability of the transcript or may facilitate cytoplasmic transport.

g. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

h. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is calorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

2. Transformation Techniques

In some instances it may be desirable to introduce recombined nucleic acids, created by the invention, into a host cell. A host cell may be "transfected" or "transformed," which refers to a process by which exogenous nucleic acid is transferred or introduced into the host cell. A transformed cell includes the primary subject cell and its progeny. Suitable methods for nucleic acid delivery for transformation of an organelle, a cell, a tissue or an organism for use with the current invention are believed to include virtually any method by which a nucleic acid (e.g., DNA) can be introduced into an organelle, a cell, a tissue or an organism, as described herein or as would be known to one of ordinary skill in the art. Such methods include, but are not limited to, electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985). Through the application of techniques such as these, organelle(s), cell(s), tissue(s) or organism(s) may be stably or transiently transformed.

3. Cells

In certain embodiments, at least one newly synthesized nucleic acid may be transfected into at least one organelle, cell, tissue or organism. In particular aspects, a newly synthesized nucleic acid is transcribed, and in more specific aspects, translated into a protein, polypeptide or peptide in the at least one organelle, cell, tissue or organism. In certain embodiments, a resulting population of transformed cells will contain a number of recombinant nucleic acids having random mutations. The mixed population may be tested to identify members containing a desired recombinant nucleic acid. The method of testing will depend on the recombinant nucleic acid of interest.

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that are capable of replicating a vector and/or expressing a heterologous gene encoded by a vector. A host cell can, and has been, used as a recipient for vectors.

Host cells may be derived from prokaryotes or eukaryotes, depending upon whether the desired result is replication of the vector or expression of part or all of the vector-encoded nucleic acid sequences. Numerous cell lines and cultures are available for use as a host cell, as would be known to one of ordinary skill in the art, such as those, for example, that can be obtained through the American Type Culture Collection (ATCC), which is an organization that serves as an archive for living cultures and genetic materials. An appropriate host can be determined by one of skill in the art based on the vector backbone and the desired result.

Some vectors used may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

In certain aspects of the present invention, it is contemplated that a recombined nucleic acid may undergo homologous recombination with a nucleic acid within the host cell. This would provide additional mutations in the recombined nucleic acid. The nucleic acids within the host cell that may undergo homologous recombination with the recombined nucleic acid may include but are not limited to chromosomes, plasmids, vectors, or viral nucleic acids.

4. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available, though in certain embodiments, new expression systems may be created using the extended nucleic acids of the present invention.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

Other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide. By example, testing may consist of placing the host cells, containing a vector with a recombinant nucleic acid, under selective pressure. One skilled in the art, given knowledge of the desired nucleic acid, peptide, or protein could readily test or screen the population to identify nucleic acid fragments that confer the desired properties.

E. In Vitro Screening of Recombinant Nucleic Acids, Peptides, Polypeptides or Proteins It is also contemplated that a recombined nucleic acid may be screened in vitro for a desired property. A translated recombined or reassembled peptide, polypeptide or protein produced in vitro may be screened for a desired activity in a manner similar to those described in a previous section, or as would be known to one of skill in the art.

Transcription in vitro may be facilitated by the addition of one or more polymerase promoter sequences during the amplification step or following amplification in a separate reaction. Promoter sequences to be added to the recombined nucleic acid sequences may vary and include, but are not limited to, bacteriophage T7, T3, or SP6 RNA polymerase promoter sequences and *E. coli* RNA polymerase promoter sequences.

In a similar manner, sequences that are required for or that may enhance translation may be added to the recombined nucleic acid sequences. These may include, but are not limited to, ribosome binding sites and start codons. By example, *E. coli* extracts are commonly used for in vitro production of recombinant proteins that are encoded within an amplified nucleic acid. Additional reagents (e.g., transcription reagents) may be added to such extracts to create a complete coupled in vitro transcription/translation system. Other reagents that may facilitate protein folding or assist in protein function may also be added to the extracts.

An in vitro method for producing a peptide, polypeptide or protein encoded by the pooled, reassembled or recombined nucleic acids may be preferable to cloning and in vivo expression. In vitro generation of a peptide, polypeptide or protein libraries may be accomplished by any number of methods (Ohuchi et al., 1998). One method comprises dilution and separation of the pool of recombined nucleic acids into numerous pools, each containing fewer nucleic acids, followed by amplification of the individual members of each new pool of recombined nucleic acids, further followed by using the products of the amplification reactions in any combination of in vitro transcription and in vitro translation reactions that results in the production of a peptide, polypeptide or protein.

In another embodiment, groups of specific members of the original pool of recombined nucleic acids may be amplified in a mixture, thereby resulting in a pool of multiple proteins, after in vitro transcription and in vitro translation.

It may be desirable to perform in vitro transcription without in vitro translation. Transcripts produced in vitro may be screened in vitro or introduced into a host cell for screening or for in vivo translation. More specifically, the pool of recombined nucleic acids generated by the described invention may be quantified by methods known to those skilled in the art (e.g., spectrophotometry, fluorometry) and diluted and separated in such a manner that a theoretically determined number of individual recombined nucleic acid molecules would be present in each of the numerous smaller pools that would be used in a single amplification. In a preferred embodiment, this process would result in the specific amplification, individually, of each member of the original pool of recombined nucleic acids.

The methods described above may be adapted to high-throughput applications. For high throughput amplification, in vitro transcription, and in vitro translation, 96-, 384-, and 1536-well, or any other multi-well plates or reaction vessels may be used.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. As can be appreciated from the disclosure above, the present invention has a wide variety of applications. Accordingly, the following examples are offered by way of illustration, not by way of limitation. Those of skill in the art should, in light of the present disclosure, appreciate that many changes can be made in the specific embodiments which are disclosed and still obtain a like or similar result without departing from the spirit and scope of the invention.

EXAMPLE 1

Recombinatorial Nucleic Acid Synthesis with a Chain-Terminating Agent

In one aspect of the present invention a primer nucleic acid can be annealed to one or more template nucleic acids (e.g., templates encoding enzymes). The template nucleic acid(s) may be resistant to exonucleolytic degradation due to the presence of one or more blocking groups in its sequence. For example, an oligonucleotide containing 3' nucleotides with α-phosphorothioate linkages could be ligated to the 3' ends of the template nucleic acids to make them resistant to degradation. The primer nucleic acid is extended in the presence of four chain-terminating agents (e.g., ddATP, ddCTP, ddGTP, ddTTP) using a DNA polymerase and appropriate salts, energy sources, nucleotides, etc., as would be known to one of skill in the art. Nucleic acid extension ladders complementary to each template nucleic acid in the reaction mixture and varying by one nucleotide increments, are produced as each of the ddNTPs are incorporated into the newly synthesized extension products.

The extension ladders are then treated (e.g. with a 3' exonucleolytic enzyme such as Exonuclease III) to remove the terminal dideoxynucleotides. The extension ladders and templates are then denatured and re-annealed. Extension ladder members produced in the previous extension may anneal to the same or to a different template nucleic acid if one is present in the reaction mixture. The previously extended nucleic acids are extended again, usually in the presence of the chain-terminating agents to stop extension at various points on the second template nucleic acid. A plurality of template nucleic acids or a template pool may be in the reaction mixture to produce the maximum variability in the sequences of each of the extension products in each cycle of extension.

The process of stopping extension with chain-terminating agents, removing the agents from the extended nucleic acids, denaturing the extended nucleic acids and the template nucleic acids and annealing the extended nucleic acids to another template nucleic acid is repeated until extended nucleic acids of desired length and/or sequence variability are created. The extended nucleic acids may be extended a final time without any chain-terminating agents to achieve a greater degree of length uniformity among the extended nucleic acids.

A plurality of mutant extended nucleic acids can be thus produced. The extended nucleic acids may be mutated or chimerized at each nucleotide position relative to the first template nucleic acid.

In another aspect of the present invention, a length-altering agent may be used instead of or in combination with a chain-terminating agent to shorten the length of an extended nucleic acid. Length-altering agents may comprise one or more chemical and/or enzymatic agents or reactions that shorten the length of an extended nucleic acid, and examples of which (e.g., at least one ribonucleotide incorporated into an extended nucleic acid, Maxam and Gilbert reactions, etc.) are described herein.

EXAMPLE 2

Producing Recombined Proteins with a Desired Property

A family of proteins from different species can easily be identified with a sequence database search using BLAST (Altschul et al, 1990). Based on these findings, if the sources of the genomic DNAs are available, the wild-type genes encoding these proteins can then be amplified by PCR™ and isolated. Additionally, the wild-type genes may be mutagenized using error-prone PCR™, or the methods of the present invention, and a library of mutant genes created. In certain embodiments, a single template sequence may be used to mutagenize the sequence, however, it may be desirable to use multiple template sequences to enhance sequence diversity through recombinatorial synthesis (i.e., extending a nucleic acid using one template, then continuing the extension with one or more different templates). Selection or screening of a mutant library for recombinant clones that encode a desired activity may provide useful template genes for further cycles of error-prone PCR™ and/or the method of the invention, library construction, and recombinant selection. Eventually, a collection of clones with genes encoding proteins that have the desired properties or that have improvements toward the desired properties may be assembled. Construction of genes that encode proteins with even greater enhancement of the desired properties may be realized by recombination of the genes from this collection of clones.

This recombination may be performed by the methods of the invention described herein, or as would be known to one of skill in the art. For example, the mutagenized genes may be used as template nucleic acids. The genes could be cloned into an M13 vector, preferably in both orientations using M13mp18 and M13mp19, or they could be cloned into any appropriate vector in one or both orientations. Nucleic acid extension ladders would be created by initiating nucleic acid synthesis from a primer (e.g., a M13 universal primer) that anneals to a region of vector-derived sequence. Such a primer may include restriction endonuclease sites and biotin moieties that would simplify purification of the recombinant nucleic acid strands derived from the invention (e.g., capture of extension products by magnetic bead affinity purification (Dynal, Oslo, Norway). Different combinations of the mutagenized genes may be used as templates in the method of the invention.

After several cycles (e.g., 5–500) of (a) nucleic acid ladder extension with dNTPs and ddNTPs, (b) Exonuclease III treatment, (c) denaturation, (d) annealing, and/or (e) re-extension, the recombined nucleic acids that are the final products are filled-in completely (i.e., re-extended with out a length-altering agent) and captured. The resulting recombined genes may then be amplified for cloning by PCR™, using flanking primers derived from vector sequences or novel PCR primers with various sequence attributes. Such additional sequences may include, for example, sequences that function as bacteriophage RNA polymerase promoters, sequences that encode polyhistidine tags, and sequences for restriction endonuclease sites. The amplified products may be cloned into suitable vectors or hosts for selection and screening of recombinants with desired properties.

It is also contemplated that the recombined nucleic acids can be diluted prior to amplification (e.g., a concentration of 1–10 copies/reaction) so as to obtain each recombined nucleic acid species individually or to obtain pools of recombined nucleic acids with a limited number of individual species. These separated recombined nucleic acids or small pools may be amplified by PCR™ and introduced directly into a coupled in vitro transcription/translation system for high throughput and automated screening of novel proteins. For example, one system for translation that can be used is the *E. coli* S30 fraction or a modified form of this fraction (ProteinScript Pro, Ambion, Inc. Austin, Tex.). In this manner, recombined genes encoding proteins with the desired properties may be easily assayed and identified and subjected again to the methods of the invention in an iterative manner, so as to produce even further recombined proteins that may display even more enhancement in the desired properties.

EXAMPLE 3

Cleavage of Dideoxynucleotides from the 3' Terminus of Extended Nucleic Acids In this example, the inventors demonstrate that Exonuclease III cleaves a dideoxynucleotide from a recessed 3'end of a nucleic acid. The ability of an exonuclease to cleave all four dideoxyribonucleotides (ddATP, ddCTP, ddGTP, ddTTP) was also demonstrated.

A DNA sequencing kit, which utilizes [α-$^{33}$P] dideoxynucleotides (Thermo Sequenase Radiolabeled Terminator Cycle Sequencing Kit) was used to generate a pool of terminated nucleotide chains. Each terminated nucleic acid contains a single [α-$^{33}$P] dideoxynucleotide at the 3' terminus. For each set of synthesis reactions, a circular plasmid (pUC18, 200 ng) (Yanisch-Perron, C. et al., 1985), a primer nucleotide (23-mer, 2 pmol; SEQ ID NO:1), polymerase (Thermo Sequenase DNA Polymerase, 8U), and reaction buffer (1X reaction buffer is 26 mM Tris-Cl, pH 9.5, 6.5 mM MgCl$_2$) were mixed and divided equally among four 0.2 ml tubes. Each tube contained one [α-$^{33}$P] ddNTP (approx. 0.02 μM) and all four dNTPs (approx. 2 μM each). The pool of terminated nucleotide chains was produced by incubating mixtures in tubes in a PE GeneAmp 2400 for 3 minutes at 95° C. followed by 2 cycles of 95° C. for 30 seconds, 55° C. for 30 seconds, and 72° C. for 120 seconds. Following the second cycle, 100U of Exonuclease III (0.5 μl) was added to each tube of one set of four tubes and distilled deionized water (0.5 μl) was added to each tube of another set of four tubes, and all tubes were incubated for an additional 120 seconds at 37° C. Reactions were stopped by the addition of EDTA and gel loading dye.

The different reaction products were separated on a 6% polyacrylamide gel made with 8M urea and examined by autoradiography. No radiolabeled nucleic acids remained in the exonuclease treated reactions.

This example demonstrates that extended strands can be synthesized with randomly incorporated nucleic acid analogs, and then cleaved at these analogs to create an extension ladder.

EXAMPLE 4

Limited Exonucleolytic Cleavage of One Nucleic Acid Strand in a Double-Stranded Nucleic Acid This example demonstrates a method to determine conditions for a limited exonucleolytic cleavage of a nucleic acid strand of a double stranded nucleic acid molecule.

Two oligonucleotides were synthesized. The template oligonucleotide (SEQ ID NO:2) was synthesized with four α-phosphorothioate dNMPs at the 3' end to protect it from exonucleolytic degradation. The primer oligonucleotide (SEQ ID NO:3) was synthesized to be complementary to the template oligonucleotide with a recessed 3' terminus. [γ-$^{32}$P]-end-labeled primer oligonucleotide (0.5 pmol) and template oligonucleotide (1 pmol) were incubated in the buffer described in Example 1. The mixture was heated to 90° C. for 3 minutes, cooled to 28° C. and held for 3 minutes, then warmed to 37° C. Dilutions of Exonuclease III (0.02 U–0.0002 U) were prepared in the same buffer and added to the mixtures in a volume of 2 μl. A control tube received 2 μl of buffer only. Mixtures were allowed to incubate at 37° C. for one minute before the addition of EDTA to stop the reactions. Reaction products for 0.002 U, 0.02 U and 0 U exonuclease III were separated on a 15% polyacrylamide 8M urea gel and examined by autoradiography. No degradation of the labeled primer oligonucleotide was observed in the control reaction. Limited degradation was observed in the reaction with 0.002 U Exonuclease III.

This example demonstrates that Exonuclease III can be diluted to a concentration that will result in a limited exonuclease cleavage of a double stranded nucleic acid, thereby allowing for removal of a limited number of terminal nucleosides, and preventing excessive degradation of the nucleic acid.

EXAMPLE 5

Exonucleolytic Cleavage of a Dideoxynucleotide and Extension from the Resulting 3' Terminus This example demonstrates exonucleolytic cleavage of a dideoxynucleoside from a nucleic acid, inhibition of extensive degradation of the nucleic acid by internal phosphorothioate linkages, and subsequent extension from the resulting 3'terminus.

Two oligonucleotides were synthesized. The template oligonucleotide (SEQ ID NO:4) was synthesized with four α-phosphorothioate dNMPs at the 3'end to protect it from exonucleolytic degradation. The primer oligonucleotide (SEQ ID NO:5) was synthesized to be complementary to the template oligonucleotide with a recessed 3' terminus. The 3' nucleotide of the primer oligonucleotide was a dideoxy CMP. The 6$^{th}$ through 8$^{th}$ nucleotides from the 3' end of the primer oligonucleotide were α-phosphorothioate dNMPs.

[γ-$^{32}$P]-end-labeled primer oligonucleotide (1.0 pmol) and template oligonucleotide (10 pmol) were incubated in the buffer described in Example 1, or in 40 mM Tris-Cl, pH 7.5, 20 mM MgCl$_2$, 50 mM NaCl. The mixture was heated to 90° C. for 3 minutes, cooled to 50° C. and held for 3 minutes, then cooled to 37° C.

Exonuclease III (2 U) was prepared in one of the two buffers and added to the mixtures in a volume of 1 μl. A control tube received 1 μl of buffer only. Mixtures were allowed to incubate at 37° C. for five minutes. Prior to nucleic acid synthesis, the exonucleolytic activity was destroyed. Mixtures were heated to 80° C. and held for 10 minutes then cooled to 50° C. Thermo Sequenase DNA polymerase (4U) a mixture of all four dNTPs (12–14 μM final concentration), and NaCl (3–4 mM final concentration) were added to some mixtures. Those were held at 50° C. for 10 minutes.

Other mixtures were held at 50° C. for 3 minutes, transferred to ice and held for 5 minutes, then transferred to room temperature. Sequenase Version 2.0 DNA Polymerase (3.25 U), dNTPs (12–14 μM final concentration), and NaCl (3–4 mM final concentration) were added to those and mixtures were incubated at room temperature for 5 minutes.

Reaction products were separated on a 20% polyacrylamide 8M urea gel and examined by autoradiography. Exonuclease treatment of annealed primer and template oligonucleotides resulted in degradation of primer oligonucleotides (with a terminal ddCMP) from 24 nucleotides in length to 19 nucleotides in length. The 3' nucleotide of the 19 mer is attached to the 18$^{th}$ nucleotide through a phosphorothioate linkage. After heating to destroy the exonucleolytic activity, nucleic acid synthesis from the newly created 3' terminus of the 19-mer was observed. The newly synthesized products were primarily 28 nucleotides in length, the same length of the template oligonucleotide.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Altschul et al., *J. Mol. Biol.* 215:403–410, 1990.
Ambrose, B. J. B. and Pless, R. C. *Methods Enzymol.* 152:522–538, 1987.
Arkin, A. & Youvan, D. C., *PNAS USA* 89:7811–7815, 1992.
Barcak, G. and Wolf, R. E. Jr. *Gene.,* 49:119–128, 1986.
Breaker R. R. and Joyce G. F. *J. Mol Evol.* 40(6):551–558, 1995.
Caldwell and Joyce, *PCR Methods and Applications* 2:28–33, 1992.
Carbonelli et al., *FEMS Microbiol Lett.* 177(1):75–82, 1999.
Chandler et al., *Proc Natl Acad Sci USA.* 94(8):3596–3601, 1997.
Chang et al., *Nature Biotechnology* 17:793–797, 1999.
Chapman K. B. and Szostak J. W. *Chem Biol.* 2(5):325–333, 1995.
Chemical and Engineering News, September 13, p 40, 1999.
Chen and Okayama, *Mol. Cell. Biol.* 7:2745–2752, 1987.
Chowrira et al., *J. Biol. Chem.,* 269:25856–25864, 1994.
Cocea, L. *Biotechniques.* 23(5):814–816, 1997.
Crameri et al., *Nature* 391:288–291, 1998.
Crameri et al., *Nature Biotechnology* 14:315–319, 1996.
Current Protocols in Molecular Biology. Ed. F. M. Ausubel et al., 1996.
Eun, H-M., Enzymology Primer for Recombinant DNA Technology, Academic Press: San Diego. Chapter 3 pp. 219–220, 1996.
Fechheimer et al., *Proc. Natl. Acad. Sci. USA* 84:8463–8467, 1987.
Foder et al., *Science,* 251:767–773, 1991.
Fraley and Fornari Kaplan, *Proc. Nat'l. Acad. Sci. USA* 76:3348–3352, 1979.
Gish & Eckstein, *NAR Symp.* Ser. No. 18:253–256, 1987.
Gopal, *Mol. Cell. Biol.,* 5:1188–1190, 1985.
Graham and Van Der Eb, *Virology,* 52:456–467, 1973.
Hager A. J. and Szostak J. W. *Chem Biol.* 4(8):607–617, 1997.
Hager et al., *Chem Biol.* 3(9):717–725, 1996.
Holeman et al., *Fold Des.* 3(6):423–431, 1998.
Kaeppler et al., *Plant Cell Reports* 9: 415–418, 1990.
Kaneda et al., *Science,* 243:375–378, 1989.
Kato et al., *J. Biol. Chem.,* 266:3361–3364, 1991.
Labeit et al., *DNA* 5:173–177, 1986.
Lee et al., *Nat Struct Biol.* 7(1):28–33, 2000.
Leung et al., *Technique* 1:11–15, 1989.
Levenson et al., *Hum Gene Ther.* 20;9(8):1233–1236, 1998.
Lieber and Strauss, *Mol. Cell. Biol.,* 15: 540–551, 1995.
Lohse P. A. and Szostak J. W. *Nature.* 30;381(6581):442–444, 1996.
Longo et al., *Gene* 93:125–128, 1990.
Lorsch J. R. and Szostak J. W. *Biochemistry.* 34(46):15315–15327, 1995.
Macejak and Sarnow, *Nature,* 353(6339):90–94, 1990.
Maxam & Gilbert, Methods *Enzymology* 65:499, 1980.
Messing & Vieira, *Gene* 19:269, 1982.
Moore & Arnold, *Nature Biotechnology* 14:458–467, 1996.
Moore et al., *J. Molecular Biol.* 272:336–347, 1997.
Nicolau and Sene, *Biochem. Biophys. Acta,* 721:185–190, 1982.
Nicolau et al., 149:157–176, 1987.
Nixon et al., *Trends in Biotech.* 16:258–264, 1989.
Ohuchi, S. et al., *NAR* 26:4339–4346, 1998.
Oliphant, A. R. et al., *Gene* 44:177–183, 1986.
Omirulleh et al., *Plant Mol. Biol.,* 21:415–28, 1993.
Ostermeier et al., *Nature Biotechnology* 17:1205–1209, 1999a.
Ostermeier et al., *PNAS* 96:3562–3567, 1999b.
PCT Application No. WO 92/20702
PCT Application No. WO 94/09699
PCT Application No. WO 95/06128
PCT Application No. WO 98/42832
PCT Application No. WO 99/29902
Pelletier and Sonenberg, *Nature,* 334(6180):320–325, 1988.
Pompon & Nicolas, *Gene* 83:15–24, 1989.
Pompon et al., *Gene* 83:15–24, 1989.
Potrykus et al., *Mol. Gen. Genet.,* 199:183–188, 1985.
Rippe et al., *Mol Cell Biol.,* 10:689–695, 1990.
Sambrook et al., In: *Molecular Cloning: A Laboratory Manual,* Vol. 1, Cold Spring Harbor Laboratory Press, Cold Spring Harbor, N.Y., Ch. 7,7.19–17.29, 1989.
Scheit, *Nucleotide Analogs* John Wiley, New York, 1980
Schulga et al., *NAR* 22:3808–3810, 1994.
Shao et al., *NAR* 26:681–683, 1998.
Skalski et al., *Biochem. Pharmacol.* 50:815–821, 1995.
Stemmer, *Nature* 370:389–391, 1994.
Stemmer, *PNAS* 91:10747–10751, 1994.
U.S. Pat. No. 4,659,774
U.S. Pat. No. 4,683,202
U.S. Pat. No. 4,684,611
U.S. Pat. No. 4,816,571
U.S. Pat. No. 4,879,236
U.S. Pat. No. 4,952,500
U.S. Pat. No. 4,959,463
U.S. Pat. No. 5,141,813
U.S. Pat. No. 5,264,566
U.S. Pat. No. 5,302,523
U.S. Pat. No. 5,322,783
U.S. Pat. No. 5,384,253
U.S. Pat. No. 5,428,148
U.S. Pat. No. 5,464,765
U.S. Pat. No. 5,538,877
U.S. Pat. No. 5,538,880
U.S. Pat. No. 5,539,082
U.S. Pat. No. 5,550,318
U.S. Pat. No. 5,554,744
U.S. Pat. No. 5,563,055
U.S. Pat. No. 5,563,055
U.S. Pat. No. 5,574,146
U.S. Pat. No. 5,582,981
U.S. Pat. No. 5,591,616
U.S. Pat. No. 5,602,244
U.S. Pat. No. 5,610,042
U.S. Pat. No. 5,714,331
U.S. Pat. No. 5,719,262

U.S. Pat. No. 5,736,336
U.S. Pat. No. 5,756,291
U.S. Pat. No. 5,766,855
U.S. Pat. No. 5,773,571
U.S. Pat. No. 5,780,610
U.S. Pat. No. 5,786,461
U.S. Pat. No. 5,792,613
U.S. Pat. No. 5,840,867
U.S. Pat. No. 5,871,986
U.S. Pat. No. 5,891,625
U.S. Pat. No. 5,925,565
U.S. Pat. No. 5,928,906
U.S. Pat. No. 5,935,819
U.S. Pat. No. 4,521,509
U.S. Pat. No. 4,521,509
U.S. Pat. No. 5,605,793
U.S. Pat. No. 5,811,238
U.S. Pat. No. 5,830,721
U.S. Pat. No. 5,965,408

Vita, C., *Current Opinion in Biotechnology* 8:429–434, 1997.
Weber et al., *NAR* 11:5661–5669, 1983.
Wilson C. and Szostak J. W. *Nature.* 374(6525):777–782, 1995.
Wong et al., *Gene,* 10:87–94, 1980.
Zhao et al., *NAR* 25:1307–1308, 1997.
Zhao et al., *Nature Biotechnology* 16:258–261, 1998.

What is claimed is:

1. A method for creating a plurality of nucleic acids comprising the steps of:
  (a) annealing a plurality of a defined first primer nucleic acid to a plurality of at least one first single stranded template nucleic acid,
  (b) performing a first extension by extending the first primer nucleic acid employing the first template nucleic acid in the presence of at least one dideoxynucleotide or a dideoxynucleotide comprising a nucleotide analog, wherein the dideoxynucleotide or dideoxynucleotide comprising a nucleotide analog is incorporated into the extended nucleic acid, to form a plurality of first extended nucleic acids having essentially identical 5' ends and variable 3' ends,
  (c) denaturing the first extended nucleic acids from the first template nucleic acid,
  (d) modifying or removing the dideoxynucleotide or dideoxynucleotide comprising a nucleotide analog from the first extended nucleic acids,
  e) annealing the first extended nucleic acids to a plurality of at least a second single stranded template nucleic acid whose sequence is not identical to the first template nucleic acid, and
  f) performing a second extension by extending the extended nucleic acid employing the second template nucleic acid to form a plurality of twice extended nucleic acids having essentially identical 5' ends.

2. The method of claim 1, wherein the second extension is performed in the presence of at least one dideoxynucleotide or dideoxynucleotide analog, wherein the dideoxynucleotide or dideoxynucleotide comprising a nucleotide analog is incorporated into the extended nucleic acid, to form a plurality of twice extended nucleic acids having essentially identical 5' ends and variable 3' ends.

3. The method of claim 2, further comprising:
  (a) modifying or removing the dideoxynucleotide or dideoxynucleotide comprising a nucleotide analog from the twice extended nucleic acids,
  (b) denaturing the twice extended nucleic acid from the second template nucleic acid
  (c) annealing the twice extended nucleic acid to a third template nucleic acid, and
  (d) performing a third extension by extending the twice extended nucleic acid employing the third template nucleic acid to form a thrice extended nucleic acid.

4. The method of claim 3, further comprising adding at least one dideoxynucleotide or dideoxynucleotide comprising a nucleotide analog before or during the third extension.

5. The method of claim 3, further comprising at least one additional series of denaturing from a template, annealing to a further template, and performing of extension.

6. The method of claim 5, further defined as comprising between one and five hundred additional series of denaturing from a template, annealing to a further template, and performing of extension.

7. The method of claim 1, wherein said dideoxynucleotide or dideoxynucleotide comprising a nucleotide analog is removed by at least one exonuclease.

8. The method of claim 1, wherein said first single stranded template nucleic acid or said second single stranded template nucleic acid vary in size, sequence, resistance to cleavage or resistance to exonuclease degradation.

9. The method of claim 1, wherein said plurality of first extended nucleic acids comprises an extension ladder.

10. The method of claim 9, wherein said plurality of first extended nucleic acids vary in length, sequence, resistance to cleavage or resistance to exonuclease degradation.

11. The method of claim 10, wherein said plurality of first extended nucleic acids comprises nucleic acids of different sequence.

12. The method of claim 11, wherein said different sequence varies by one nucleotide.

13. The method of claim 10, wherein said plurality of first extended nucleic acids comprise different lengths.

14. The method of claim 13, wherein said different lengths comprise one nucleotide increments.

15. The method of claim 14, wherein said different lengths comprise more than one nucleotide increments.

16. The method of claim 1, wherein the extended nucleic acid comprises at least one partly double stranded nucleic acid or at least one fully double stranded nucleic acid.

17. The method of claim 1, wherein said defined first primer nucleic acid is resistant to cleavage or exonuclease digestion.

18. The method of claim 1, wherein said defined first primer nucleic acid is a plurality of primers.

19. The method of claim 18, wherein said plurality of primers vary in length, sequence, resistance to cleavage or resistance to exonuclease degradation.

20. The method of claim 1, wherein the first extended nucleic acid comprises the primer nucleic acid.

21. The method of claim 1, wherein said first or second extended nucleic acid is a recombinant, mutagenized or chimeric nucleic acid.

22. The method of claim 1, wherein said at least one first single stranded template nucleic acid or said at least one second single stranded template nucleic acid is a plurality of template nucleic acids.

23. The method of claim 1, further comprising the addition of at least one length-altering agent.

24. The method of claim 23, wherein the length-altering agent comprises a nucleotide, a nucleotide derivative, a nucleotide analog, a chemical treatment or a combination thereof.

25. The method of claim 24, wherein said length-altering agent comprises a nucleotide incorporated into said first or second extended nucleic acid.

26. The method of claim 25, wherein said nucleotide comprises at least one ribonucleotide.

27. The method of claim 26, wherein said length-altering agent further comprises treatment with an alkaline condition or a ribonuclease.

28. The method of claim 26, wherein said length-altering agent further comprises treatment with alkaline phosphatase and an exonuclease.

29. The method of claim 24, wherein said length-altering agent comprises a nucleotide derivative incorporated into said extended nucleic acid.

30. The method of claim 24, wherein the length-altering agent comprises a nucleotide analog incorporated into said extended nucleic acid.

31. The method of claim 30, wherein said nucleotide analog comprises at least one α-phosphorothioate nucleotide.

32. The method of claim 31, wherein said length-altering agent further comprises alkylation of said extended nucleic acid.

33. The method of claim 24, wherein the length-altering agent comprises a chemical treatment of said extended nucleic acid.

* * * * *

UNITED STATES PATENT AND TRADEMARK OFFICE
CERTIFICATE OF CORRECTION

PATENT NO. : 6,994,963 B1 Page 1 of 1
APPLICATION NO. : 09/613535
DATED : February 7, 2006
INVENTOR(S) : Murphy et al.

It is certified that error appears in the above-identified patent and that said Letters Patent is hereby corrected as shown below:

In column 44, line 50 of claim 10, please replace "claim 9" with --claim 1-- therefor.

Signed and Sealed this

Twenty-first Day of November, 2006

JON W. DUDAS
*Director of the United States Patent and Trademark Office*